(12) United States Patent
Pananen et al.

(10) Patent No.: US 11,806,505 B2
(45) Date of Patent: Nov. 7, 2023

(54) SINGLE-SITE INSERTION OF MULTIPLE MEDICAL DEVICES

(71) Applicant: Medtronic MiniMed, Inc., Northridge, CA (US)

(72) Inventors: Jacob E. Pananen, Santa Monica, CA (US); Ellis Garai, Studio City, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 194 days.

(21) Appl. No.: 17/109,600

(22) Filed: Dec. 2, 2020

(65) Prior Publication Data

US 2022/0168502 A1 Jun. 2, 2022

(51) Int. Cl.
*A61M 5/158* (2006.01)
*A61M 5/162* (2006.01)
*A61M 5/172* (2006.01)

(52) U.S. Cl.
CPC ............ *A61M 5/158* (2013.01); *A61M 5/162* (2013.01); *A61M 5/1723* (2013.01); *A61M 2005/1585* (2013.01); *A61M 2005/1586* (2013.01); *A61M 2005/1726* (2013.01); *A61M 2205/103* (2013.01); *A61M 2230/201* (2013.01)

(58) Field of Classification Search
CPC .... A61M 5/158; A61M 5/162; A61M 5/1723; A61M 2005/1585; A61M 2005/1586; A61M 2005/1726; A61M 2205/103; A61M 2230/201; A61M 5/3295; A61M 5/3298; A61M 5/142; A61M 5/14244; A61M 5/14248; A61M 2005/14252; A61M 2005/14256; A61M 2005/1426; A61M 2005/14268
See application file for complete search history.

(56) References Cited

U.S. PATENT DOCUMENTS

| | | |
|---|---|---|
| 8,641,670 B2 | 2/2014 | Yodat et al. |
| 8,679,062 B2 | 3/2014 | Yodat et al. |
| 8,747,363 B2 | 6/2014 | Nielsen et al. |

(Continued)

FOREIGN PATENT DOCUMENTS

WO 2020051211 A2 3/2020

OTHER PUBLICATIONS

U.S. Appl. No. 16/893,141, filed Jun. 4, 2020, naming inventors Chiu et al.

(Continued)

*Primary Examiner* — Kami A Bosworth
*Assistant Examiner* — Antarius S Daniel
(74) *Attorney, Agent, or Firm* — Fortem IP LLP; Suzannah Beeman; Mary L. Fox

(57) ABSTRACT

In some embodiments, an apparatus may comprise a first insertion needle and a second insertion needle. The first insertion needle may be configured to carry a first medical device (e.g., a sensor) through an opening in an apparatus housing. The second insertion needle may be configured to carry a second medical device (e.g., a cannula) along a curved path that passes through the opening in the apparatus housing such that a distal end of the first medical device becomes increasingly displaced from the distal end of the second medical device as the distal end of the second medical device is carried along the curved path.

20 Claims, 7 Drawing Sheets

(56) References Cited

U.S. PATENT DOCUMENTS

| | | |
|---|---|---|
| 9,545,477 B2 | 1/2017 | Chong et al. |
| 9,610,402 B2 | 4/2017 | Yavorsky et al. |
| 9,839,747 B2 | 12/2017 | Smith et al. |
| 9,943,643 B2 | 4/2018 | Constantineau et al. |
| 10,092,691 B2 | 10/2018 | Searle et al. |
| 10,195,342 B2 | 2/2019 | Cole et al. |
| 10,220,145 B2 | 3/2019 | Jennewine |
| 10,413,183 B2 | 9/2019 | Antonio et al. |
| 10,413,658 B2 | 9/2019 | Gillett et al. |
| 10,441,717 B2 | 10/2019 | Schmid et al. |
| 10,463,787 B2 | 11/2019 | Shor et al. |
| 10,569,011 B2 | 2/2020 | Dilanni et al. |
| 10,596,295 B2 | 3/2020 | Larson et al. |
| 2006/0253085 A1 | 11/2006 | Geismar et al. |
| 2012/0245536 A1 | 9/2012 | Gerber et al. |
| 2015/0164545 A1 | 6/2015 | Gyrn |
| 2015/0290391 A1* | 10/2015 | Schmid .............. A61B 5/14532 604/504 |
| 2017/0021137 A1 | 1/2017 | Cole |
| 2017/0232191 A1 | 8/2017 | Smith et al. |
| 2019/0160225 A1 | 5/2019 | Verlaak et al. |
| 2020/0023122 A1 | 1/2020 | McCullough et al. |
| 2020/0230313 A1* | 7/2020 | Mojarrad ............... A61M 5/142 |
| 2021/0178058 A1* | 6/2021 | Scott ........................ A61M 5/46 |
| 2021/0220549 A1* | 7/2021 | Lanigan ............ A61M 5/14232 |
| 2022/0096754 A1* | 3/2022 | Blancke ................ A61M 5/315 |
| 2022/0105267 A1* | 4/2022 | Cardinali ........... A61M 5/14248 |

OTHER PUBLICATIONS

U.S. Appl. No. 17/151,385, filed Jan. 18, 2021, naming inventors Pananen et al.

U.S. Appl. No. 17/150,368, filed Jan. 15, 2021, naming inventors Pananen et al.

* cited by examiner

SINGLE-SITE INSERTION OF MULTIPLE MEDICAL DEVICES

TECHNICAL FIELD

This disclosure relates generally to insertion techniques for medical devices.

BACKGROUND

Certain diseases or conditions may be treated, according to modern medical techniques, by delivering a medication fluid or other substance to the body of a patient, either in a continuous manner or at particular times or time intervals within an overall time period. For example, diabetes is often treated by delivering defined amounts of insulin to the patient at appropriate times. Some modern systems employ programmable fluid infusion devices (e.g., insulin pumps) to deliver controlled amounts of insulin to a patient via a cannula. Moreover, in certain instances, it may also be desirable for the patient to receive information from a physiological characteristic monitor, such as a glucose monitor. In these instances, the physiological characteristic monitor and the cannula are often separately coupled to the user's anatomy at different insertion sites so that insulin delivered via the cannula does not interfere with measurements by the physiological characteristic monitor.

BRIEF SUMMARY

The disclosure generally relates to a first insertion needle and a second insertion needle configured to respectively carry a first medical device and a second medical device through an opening in an apparatus housing. The second insertion needle may be configured to carry the second medical device along a curved path that passes through the opening such that a distal end of the first medical device becomes increasingly displaced from a distal end of the second medical device as the distal end of the second medical device is carried along the curved path.

The details of one or more examples are set forth in the accompanying drawings and the description below. Other features, objects, and advantages will be apparent from the description and drawings, and from the claims.

BRIEF DESCRIPTION OF THE DRAWINGS

Although different figures use the same numerals, the figures should not be construed as depicting the same elements. For example, element 100 of FIG. 2 is not necessarily the same as element 100 of FIG. 3.

DETAILED DESCRIPTION

Figure 1:
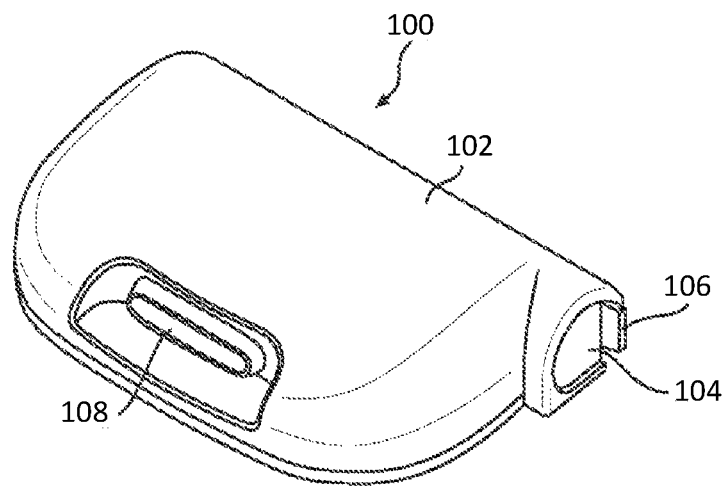
FIG. 1 is a top perspective view of an example of a therapy delivery device.

The disclosure describes an insertion device configured to at least partially implant a first medical device (e.g., a sensor) and a second medical device (e.g., a cannula) within a patient via the same insertion site on the patient. At least the second medical device may be inserted into the patient along a curved path that passes through the insertion site and into the patient. Inserting the second medical device along the curved path enables the distal end of the second medical device to become increasingly separated from the distal end of the first medical device. Among other benefits, the techniques implemented by the insertion device enable reduction or avoidance of interference between the medical devices while decreasing patient discomfort.

The insertion device may facilitate use of a therapy delivery device (e.g., a fluid infusion device) configured to provide a therapeutic fluid to a user (e.g., a patient) and monitor a physiological characteristic of the user. For example, the first medical device may be a fluid delivery cannula configured to deliver a fluid (e.g., insulin) to the user. The second medical device may be an analyte sensor (e.g., a glucose sensor) configured to detect a physiological characteristic of the user (e.g., a glucose level). The insertion device may be configured to insert the first medical device and the second medical device in the user substantially concurrently. In examples, the therapy delivery device is a portable system configured to be worn by the user.

The therapy delivery device may include a housing configured to be positioned proximate to the skin of the user. In examples, the housing is configured to contact the skin of the user. The housing may be configured to be substantially secured to a location on the user in order to, for example, allow mobility to the user as the therapy delivery device administers and monitors therapies delivered to the user. For example, the therapy delivery device may be configured to allow a degree of user mobility as the therapy delivery device delivers insulin to the user through a fluid delivery cannula (e.g., the first medical device) and monitors a glucose level of the user using an analyte sensor (e.g., the second medical device). The therapy delivery device may be substantially secured to the user using any suitable arrangement. In some examples, the housing of the therapy delivery device includes an adhesive element configured to removably secure the housing to the skin of the user.

In examples, the therapy delivery device is configured such that, when positioned on the skin of the user, the user may initiate at least partial implantation of the first medical device and the second medical device. For example, the user may initiate the at least partial implantation using a manually operated button on the housing, a wireless communication to the therapy delivery device, or some other user-controlled activation.

The insertion device may be internal/external to the therapy delivery device. Stated differently, in some embodiments, the insertion device may be included within the housing of the therapy delivery device, and in some other embodiments, the insertion device may be included within a second housing that can engage and disengage the housing of the therapy delivery device as desired. The insertion device may be configured to cause a first insertion needle and a second insertion needle to extend through an opening in the therapy delivery device housing to at least partially implant the first and second medical devices in a patient. The insertion device may also be configured to subsequently withdraw the insertion needles from the patient such that the first and second medical devices remain at least partially implanted within the patient.

The first and second insertion needles may be configured to insert through and withdraw from the skin of the patient. The first insertion needle and/or second insertion needle may be configured to pierce the skin of the patient. Upon activation by the user, the insertion device may cause the first insertion needle and the second insertion needle to extend from the therapy delivery device housing to insert through the skin and/or to subsequently retract toward the therapy delivery device housing to withdraw from the skin. In some embodiments, the first insertion needle may be integrated with the first medical device such that both the needle and the medical device remain inserted in the patient. In some other embodiments, the first insertion needle may be configured to releasably carry the first medical device, such that the first insertion needle at least partially implants the first medical device during its extension and leaves the first medical device at least partially implanted within the patient during its retraction. In some embodiments, the second insertion needle may be integrated with the second medical device such that both the needle and the medical device remain inserted in the patient. In some other embodiments, the second insertion needle may be configured to releasably carry the second medical device, such that the second insertion needle at least partially implants the second medical device during its extension and leaves the second medical device at least partially implanted during its retraction. In examples, the insertion device is configured to cause the first and second insertion needles to cause at least partial implantation of the first medical device and second medical device substantially concurrently.

The insertion device may be configured to cause the first insertion needle and the second insertion needle to insert through the skin of the patient at a single insertion site on the patient. The insertion site may be a relatively small area on the skin of the patient. Using the same insertion site may reduce the number of punctures distributed over the skin. The insertion device may be configured such that the first insertion needle and the second insertion needle are inserted substantially concurrently in order to, for example, limit discomfort to the patient that might otherwise be caused by multiple insertions at different times.

Although the first insertion needle and the second insertion needle are inserted at the same insertion site on the patient, the distal end of the first medical device may become displaced from the distal end of the second medical device within the patient. In examples, the insertion device is configured to cause the first insertion needle to extend in a first direction away from the therapy delivery device housing and cause the second insertion needle to extend in a different, second direction away from the therapy delivery device housing. The displacement may reduce negative effects that may occur due to proximity between the first medical device and the second medical device. For example, displacement between the distal ends of a fluid delivery cannula and an analyte sensor may help prevent readings reported by the analyte sensor (e.g., glucose levels) from being adversely impacted by delivery of a fluid (e.g., insulin) through the fluid delivery cannula.

The therapy delivery device may include a variety of internal components configured to use the first medical device and the second medical device to provide therapy and monitor a physiological characteristic of the user. In examples, the first medical device and/or the second medical device is a fluid delivery cannula, and the therapy delivery device includes a fluid pump (e.g., an insulin pump) configured to deliver a fluid (e.g., insulin) to the user from a fluid reservoir within the therapy delivery device. The fluid reservoir may be, for example, a volume defined by a detachable fluid cartridge configured to mechanically engage a housing of the therapy delivery device and to establish a fluidic connection with the fluid pump. In examples, the therapy delivery device includes processing circuitry configured to control an operation of the fluid pump. For example, the processing circuitry may be configured to cause the fluid pump to commence, continue, and/or cease causing transportation of fluid from the fluid reservoir through the fluid delivery cannula. In examples, the first medical device and/or the second medical device is an analyte sensor configured to generate a signal indicative of a physiological characteristic of the user (e.g., a glucose level), and the processing circuitry is configured to determine the physiological characteristic using the indicative signal. In some examples, the processing circuitry is configured to control an operation of the fluid pump based on the indicative signal reported by the analyte sensor.

The insertion device may include one or more axles, and each axle may be configured to rotate around a respective longitudinal axis of rotation. Each axle may be configured to rotate in a first rotational direction and a second rotational direction around the axis of rotation, with the second rotational direction being opposite the first rotational direction. For example, an axle may be configured to cause the first insertion needle and the second insertion needle to extend away from the therapy delivery device housing to insert through the skin when the axle rotates in the first rotational direction. The axle may also be configured to cause the first insertion needle and the second insertion needle to retract toward the therapy delivery device housing when the axle rotates in the second rotational direction. In examples, a first axle may be configured to rotate around a first axis of rotation to cause the insertion and/or retraction of the first insertion needle, and a second axle may be configured to rotate around a second axis of rotation parallel to the first axis to cause the insertion and/or retraction of the second insertion needle. The first axle may be configured to rotate a first circular gear, and the second axle may be configured to rotate a second circular gear. The circular gears may be meshed such that the axles rotate in opposite directions.

The one or more axles may be configured to substantially drive the first insertion needle and the second insertion needle to insert through the skin. In examples, the first insertion needle and/or the second insertion needle defines a curved path when the one or more axles drive the first insertion needle and the second insertion needle. For example, the first insertion needle may be a curved needle substantially curving around an axle's axis of rotation. The first insertion needle may be configured such that, as the first insertion needle is driven through the skin, a distal end of the first insertion needle ("first needle distal end") substantially tunnels through subcutaneous tissue of the patient in a curved path (e.g., a circular path) relative to the axle's axis of rotation. In examples, the first insertion needle is configured such that the curved path of the first needle distal end causes the first needle distal end to be displaced from a distal end of the second insertion needle ("second needle distal end"). For example, the first insertion needle may be a curved needle having a first degree of curvature (see, for example, path S1 in FIG. 3), and the second insertion needle may be a curved needle having a second degree of curvature (see, for example path S2 in FIG. 3), that is opposite in direction but equal in magnitude to the first degree of curvature. Thus, the first and second insertion needles may puncture the skin at the same site but symmetrically diverge as they are further inserted below the skin.

In examples, one of the first insertion needle or the second insertion needle defines a path having a reduced curvature (e.g., a substantially straight path) compared to the other of the first insertion needle or the second insertion needle. For example, the second insertion needle may be a substantially straight needle configured to exhibit a linear motion relative to the therapy delivery device housing when an axle drives the first insertion needle and the second insertion needle. The second insertion needle may be configured such that, as the axle drives the second insertion needle through the skin, the second needle distal end substantially tunnels through subcutaneous tissue of the user in a straight path relative to the therapy delivery device housing. Hence, as the rotation of the axle causes insertion of the first insertion needle and the second insertion needle, the substantially curved path (for example, S1 in FIG. 3) defined by one insertion needle (e.g., first insertion needle) and the reduced curvature (e.g., substantially straight) path (for example S2 in FIG. 3) defined by the other insertion needle (e.g., the second insertion needle) causes the first needle distal end and the second needle distal end to diverge (e.g., displace) during the insertion. The divergence may cause displacement between the distal end of the first medical device and the distal end of the second medical device to increase as the first medical device and the second medical device are further inserted into the user.

An axle can be configured to impart a torque to a curved needle (e.g., the first insertion needle) in a variety of ways In examples, the axle is operatively connected to the curved needle using, for example, a strut attached to the axle and attached to the curved needle. In some examples, the axle is directly attached to the curved needle. In some examples, a surface of the axle is configured to frictionally engage a surface of the curved needle to impart the torque to the curved needle. In some examples, the axle may be configured to rotate a pinion gear meshed with a curved rack gear coupled to the curved needle. Thus, when the axle rotates around its axis of rotation, the curved needle may also rotate around the axis of rotation. The axle may be configured to impart a torque to the curved needle in a first rotational direction and/or a second rotational direction. In examples, the axle is configured to impart a torque to the curved needle in the first rotational direction to cause the curved needle to insert through the skin of the patient, and configured to impart a torque to the curved needle in the second rotational direction to cause the curved needle to withdraw from the skin of the patient.

The axle may be configured to cause a substantially straight needle (e.g., the second insertion needle) to move substantially linearly with respect to the therapy delivery device housing. The axle and the substantially straight needle may be cooperatively configured to convert a rotation of the axle to a linear movement of the substantially straight needle with respect to the therapy delivery device housing. In examples, the axle is configured to rotate a pinion gear meshed with a substantially straight rack gear coupled to the substantially straight needle, such that rotation of the pinion gear causes a linear movement of the substantially straight needle. In examples, a surface of the axle is configured to frictionally engage a surface of the substantially straight needle to cause the linear movement of the substantially straight needle.

The insertion device may include a torsion spring configured to cause an axle to rotate. For example, the insertion device may include one or more loaded torsion springs configured to become unloaded when the user activates the insertion device. In examples, the insertion device includes a first torsion spring configured to cause the axle to rotate in a first rotational direction and a second torsion spring configured to cause the axle to rotate in a second rotational direction. The insertion device may be configured such that the first torsion spring causes rotation of the axle in the first rotational direction (e.g., to insert the first insertion needle and the second insertion needle) and such that the second torsion spring subsequently causes rotation in the axle in the second rotational direction (e.g., the retract the first insertion needle and the second insertion needle).

In examples, the insertion device is configured such that a certain amount of rotation in the first rotational direction causes the second torsion spring to become loaded to subsequently cause the rotation in the second rotational direction. For example, the insertion device may be configured such that rotation in the first rotational direction applies load to the second torsion spring. Then, the second torsion spring may become unloaded to cause rotation of the axle in the second rotational direction. In some examples, the insertion device is configured to cause one or more mechanical stops engaging the second torsion spring to disengage after the certain amount of rotation in the first rotational direction such that the second torsion spring may become unloaded to cause the rotation of the axle in the second rotational direction.

Hence, the therapy delivery device may be positioned proximate to the skin of a user, and the insertion device may cause a first insertion needle and a second insertion needle to extend away from the therapy delivery device housing, to be inserted through the skin, and/or to retract toward the therapy delivery device housing for withdrawal from the skin. The first insertion needle may be configured to at least partially implant a first medical device in the user and the second insertion needle may be configured to at least partially implant a second medical device in the user. The insertion device may be operatively connected to a user input device configured to allow the user to control when the insertion device causes at least partial implantation of the first medical device and the second medical device. In examples, the first medical device is a fluid delivery cannula and the second medical device is an analyte sensor. The therapy delivery device may include a fluid pump (e.g., an insulin pump) configured to deliver a fluid (e.g., insulin) to the user, and may include processing circuitry configured to receive signals indicative of a physiological characteristic of the user (e.g., a glucose level) from the analyte sensor. The processing circuitry may be configured to control an operation of the fluid pump based on the indicative signals received from the analyte sensor. The therapy delivery device may be utilized to administer a variety of medications to a user such as, but not limited to, disease treatments, drugs to treat pulmonary hypertension, iron chelation drugs, pain medications, anti-cancer treatments, medications, vitamins, hormones, or the like.

FIG. 1 is a top perspective view of an example therapy delivery device 100 configured as a fluid infusion device.

Figure 2:
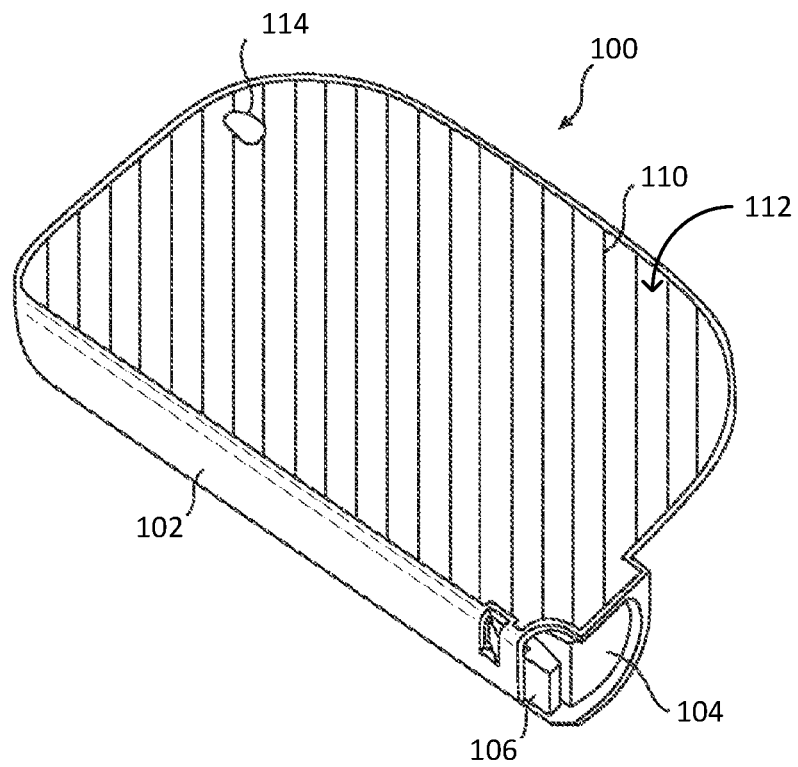
FIG. 2 is a bottom perspective view of the therapy delivery device of FIG. 1.
Figure 3:
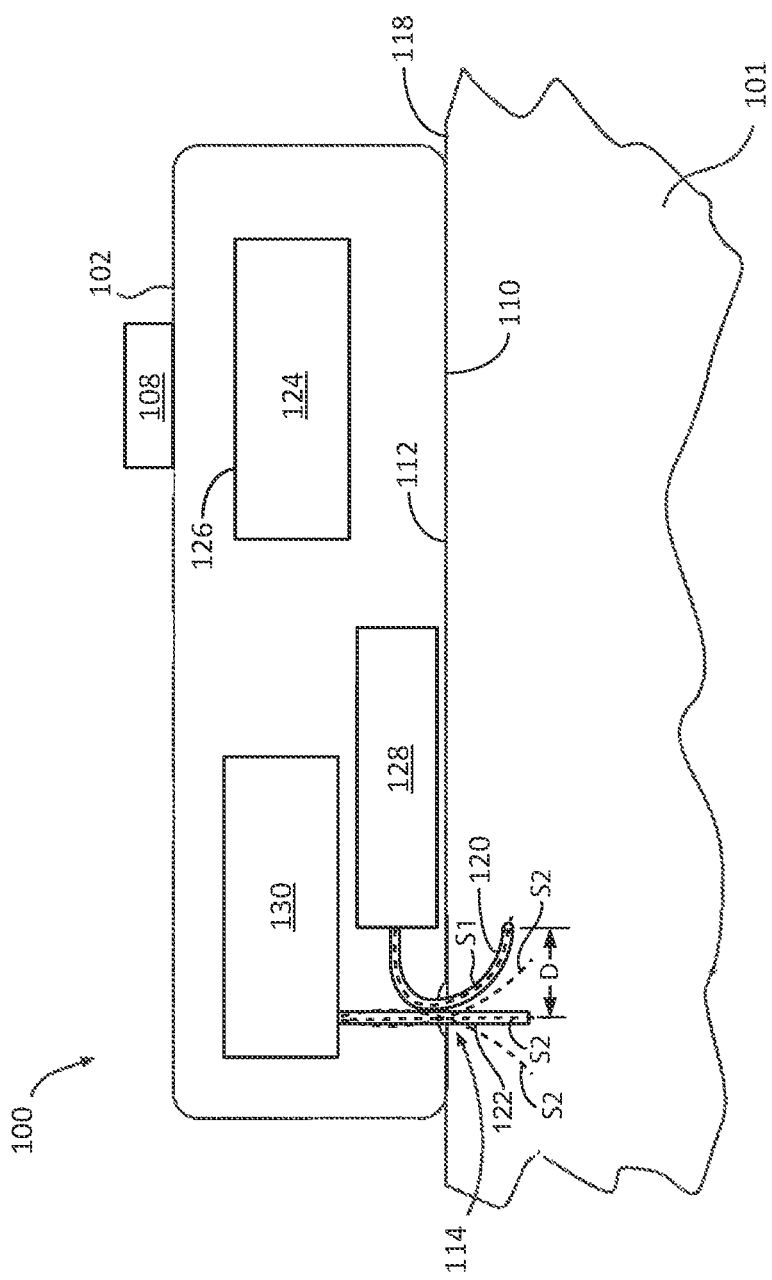
FIG. 3 is a schematic side view of an example therapy delivery device attached to the body of a user.

The fluid infusion device may be implemented as a patch pump device. FIG. 2 is a bottom perspective view of therapy delivery device 100. FIG. 3 is a schematic side view of an example therapy delivery device 100 contacting a body 101 of a user. FIGS. 1, 2, and 3 depict some possible configurations and form factors of a therapy delivery device 100. Other designs and configurations can be utilized if so desired, and the particular design aspects shown and/or described in FIGS. 1, 2, 3, and elsewhere are not intended to limit or otherwise restrict the scope or application of the examples described herein.

Therapy delivery device 100 includes a device housing 102 that may serve as a shell for a variety of internal components of therapy delivery device 100. For example, device housing 102 may mechanically support one or more internal components configured to monitor a physiological characteristic of a user and/or delivery therapy to the user. In examples, device housing 102 is configured to mechanically support one or more insertion needles configured to insert one or more medical devices into the user. Device housing 102 may mechanically support one or more components configured to cause the one or more insertion needles to insert the medical devices in the user. In some examples, device housing 102 is configured to mechanically support internal components configured to utilize and/or communicate with the medical devices for monitoring of and/or delivering therapy to the user. For example, device housing 102 may mechanically support a first insertion needle configured to insert a fluid delivery cannula into the user, a second insertion needle configured to insert an analyte sensor into the user, a fluid pump configured to cause delivery of a fluid from a fluid reservoir and through the fluid delivery cannula, and processing circuitry configured to communicate with the analyte sensor and/or the fluid pump. Device housing 102 may be configured to position therapy delivery device 100 proximate and/or in contact with the skin of the user.

In examples, device housing 102 may be configured to mechanically support a removable fluid cartridge 104 defining a fluid reservoir. Fluid cartridge 104 may be, for example, a disposable insulin cartridge. Device housing 102 may be suitably configured to receive, secure, and release fluid cartridge 104. For example, FIG. 1 and FIG. 2 depict a fluid cartridge 104 installed and substantially secured within device housing 102. Device housing 102 may be configured such that, when fluid cartridge 104 is mechanically supported by (e.g., installed in) device housing 102, a fluid pump mechanically supported by device housing 102 establishes a fluidic connection with the fluid reservoir defined by fluid cartridge 104. Device housing 102 may include a suitably shaped, sized, and configured cavity configured to engage particular physical characteristics of fluid cartridge 104. For example, the device housing 102 can include structural features that mate with or otherwise engage structural features of fluid cartridge 104.

Fluid cartridge 104 may have any shape, size, and/or configuration sufficient to engage with device housing 102. In examples, fluid cartridge 104 includes a cartridge retention mechanism 106 configured to secure fluid cartridge 104 in an installed and seated position within therapy delivery device 100. Retention mechanism 106 may mechanically engage device housing 102 to substantially lock the fluid cartridge 104 in place to maintain physical and/or fluidic connections between the fluid cartridge 104 and one or more components of therapy delivery device 100. Retention mechanism 106 may be configured to allow physical manipulation by the user to remove and/or install fluid cartridge 104.

In some embodiments, therapy delivery device 100 includes at least one user input device 108 which may be actuated by the user as needed. User input device 108 may be a manually operated button on device housing 102; circuitry configured to receive a communication (e.g., a wireless communication) from a smart phone, tablet, or other external device; and/or some other device configured for receiving user input. In examples, user input device 108 (e.g., a button) is configured to cause an insertion device to insert a first medical device and/or second medical device into the user. In some embodiments, the user input device 108 may provide a multipurpose user interface configured to initiate multiple operations of therapy delivery device 100. For example, user input device 108 may be configured to cause one or more of the following functions, without limitation: waking up the processor and/or electronics of therapy delivery device 100; triggering an insertion device to insert a first medical device (e.g., a fluid delivery cannula) and/or a second medical device (e.g., an analyte sensor) into a subcutaneous space or similar region of the user; configuring one or more settings of therapy delivery device 100; initiating delivery of medication fluid; initiating a fluid priming operation; disabling alerts or alarms generated by therapy delivery device 100; and the like. In lieu of a button, user input device 108 can employ a slider mechanism, a pin, a lever, a switch, a touch-sensitive element, or the like.

User input device 108 may be configured to receive a communication from a device remote from device housing 102 (e.g., a wireless communication) to initiate performance of one or more of the above-described functions, or other functions. In examples, therapy delivery device 100 includes more than one user input device 108 (e.g., more than one button) to initiate the various functions described above.

In examples, therapy delivery device 100 is a portable device. Therapy delivery device 100 may be a wearable device configured to be worn by the user. As depicted in FIG. 2, therapy delivery device 100 may include an adhesive element 110 or an adhesive material configured to substantially affix the device housing 102 to the body of the user. Adhesive element 110 may be configured to substantially secure therapy delivery device 100 to the skin 118 (FIG. 3) of the user. Adhesive element 110 may be located on a bottom surface of the device housing 102 such that the device housing 102 can be temporarily adhered to the skin of the user. The adhesive element 110 may cover substantially all of the lower surface (as depicted), or it can only partially cover the lower surface if so desired. Adhesive element 110 may be, for example, a piece of double-sided adhesive tape that is cut into the desired shape and size. In some examples, therapy delivery device 100 is manufactured with an adhesive liner overlying adhesive element 110, and the adhesive liner is peeled away to expose the sticky surface of adhesive element 110.

Device housing 102 may include a base surface 112 (which is covered by the adhesive element 110 in FIG. 2). Base surface 112 may be configured to serve as the user-mounting structure of therapy delivery device 100. In examples, base surface 112 includes at least one hole 114 forming an opening through device housing 102. Hole 114 may further form an opening through adhesive element 110 when adhesive element 110 covers some portion of base surface 112.

Hole 114 may be defined to accommodate passage of one or more insertion needles and medical devices from a position within device housing 102 to a position at least partially outside of device housing 102. In examples, hole 114 is configured (e.g., shaped, sized, and/or located) to accommodate passage of a first insertion needle and a first medical device (e.g., a fluid delivery cannula), and accommodate passage of a second insertion needle and a second medical device (e.g., an analyte sensor). Hole 114 may be configured to accommodate passage of the needles and medical devices from a position within device housing 102 to a position at least partially outside of device housing 102. Hole 114 may be configured to accommodate retraction of the first insertion needle and the second insertion needle from a position outside device housing 102 to a position within device housing 102. In examples, hole 114 is configured to accommodate substantially concurrent passage of the first insertion needle, the first medical device, the second insertion needle, and the second medical device. Thus, when device housing 102 is positioned proximate to the user, hole 114 may specify an insertion site on the user, and the insertion site may be shared by the first and second medical devices in that they are each inserted via the insertion site.

FIG. 3 depicts a therapy delivery device 100 in schematic form. Therapy delivery device 100 is depicted proximate to (e.g., in contact with) the skin 118 of a user. A first medical device 120 is inserted in the user and extends through hole 114 from a position within device housing 102 to a position outside of device housing 102 (e.g., a first location under the skin 118). A second medical device 122 is inserted in the user and extends through hole 114 from another position within device housing 102 to another position outside of housing 102 (e.g., a second location under the skin 118). In examples, first medical device 120 is a fluid delivery cannula configured to deliver a fluid (e.g., insulin) to the first location and second medical device 122 is an analyte sensor configured to sense a physiological characteristic (e.g., a glucose level) at the second location. Insertion device 124 is configured to insert first medical device 120 and second medical device 122 into the user such that the first location and the second location are separated by a displacement D. FIG. 3 further depicts adhesive element 110 configured to substantially secure the device housing 102 to the skin of the user.

Insertion device 124 may be configured to cause insertion of first medical device 120 and second medical device 122 within the user when, for example, the user actuates insertion device 124 using user input device 108. Thus, in some embodiments, user input device 108 may be a component of the insertion device 124. For example, user input device 108 may be a manually operated button on housing 126 of insertion device 124. Insertion device 124 may be configured to cause a first insertion needle (e.g., first insertion needle 132 (FIGS. 4, 5A-5C)) to extend through hole 114 to insert first medical device 120 (e.g., a fluid delivery cannula) into the user, and/or configured to cause the first insertion needle to retract back through hole 114 while first medical device 120 remains inserted in the user. Insertion device 124 may be configured to cause a second insertion needle (e.g., second insertion needle 134 (FIGS. 4, 5A-5C)) to extend through hole 114 to insert second medical device 122 (e.g., an analyte sensor) into the user, and/or configured to cause the second insertion needle to retract back through hole 114 while second medical device 122 remains inserted in the user. In some embodiments, insertion device 124 may be a component of therapy delivery device 100. In some other embodiments, insertion device 124 may be separate from therapy delivery device 100. For example, insertion device 124 may include a housing 126 configured to couple with device housing 102 during insertion and to detach from device housing 102 when insertion is complete.

Therapy delivery device 100 may also comprise a fluid infusion system 128 and a sensor system 130. Fluid infusion system 128 may be configured to deliver a fluid (e.g., insulin) to the user. Sensor system 130 may be configured to monitor a physiological characteristic of the user (e.g., a glucose level).

Figure 4:
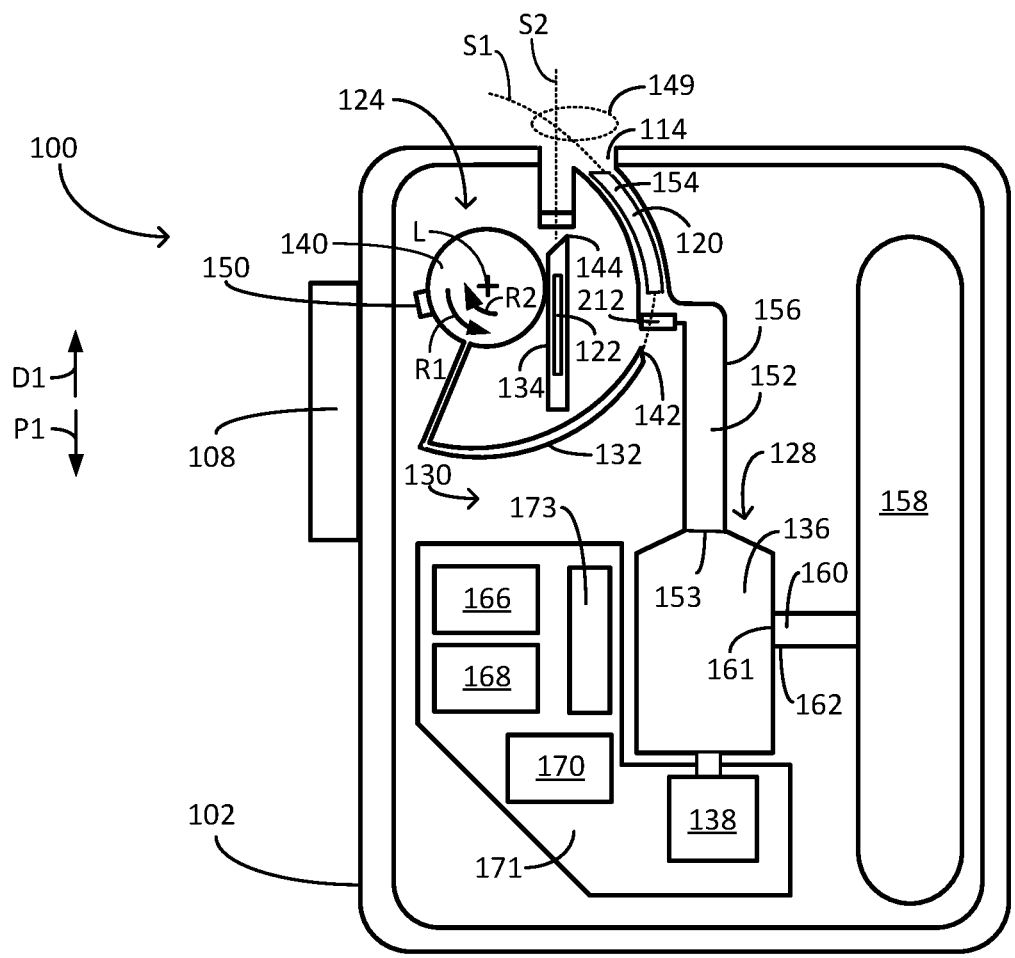
FIG. 4 is a simplified block diagram representation of an example therapy delivery device.

FIG. 4 is an example simplified block diagram representation of a therapy delivery device 100 including device housing 102, user input device 108, first medical device 120, second medical device 122, insertion device 124 including a first insertion needle 132 and a second insertion needle 134, fluid infusion system 128 including a fluid pump 136 and a pump motor 138, and sensor system 130 including a sensor interface 173. First insertion needle 132 may be configured to releasably engage first medical device 120. Second insertion needle 134 may be configured to releasably engage second medical device 122. Insertion device 124 is configured to cause first insertion needle 132 to move (e.g., generally along the path S1) to engage first medical device 120 and cause insertion of first medical device 120 in the user. Insertion device 124 is configured to cause second insertion needle 134 to move (e.g., generally along the path S2) to cause insertion of second medical device 120 in the user. Insertion device 124 may be configured to retract first insertion needle 132 and second insertion needle 134 to a position within housing 102 while first medical device 120 and second medical device 122 remain inserted in the user.

Therapy delivery device 100 may be configured to provide a fluid (e.g., insulin) to a user using, for example, first medical device 120. Therapy delivery device 100 may be configured to provide the fluid when first medical device 120 is inserted within the user (FIG. 3). Therapy delivery device 100 may be configured to monitor a physiological characteristic (e.g., a glucose level) of the user using, for example, second medical device 122. Therapy delivery device 100 may be configured to monitor the physiological characteristic when second medical device 122 is inserted within the user (FIG. 3). Insertion device 124 is configured to cause first insertion needle 132 and second insertion needle 134 to extend away from device housing 102 to insert first medical device 120 and second medical device 122 respectively into the user, and may be configured to cause first insertion needle 132 and second insertion needle 134 to retract toward housing 102 as first medical device 120 and second medical device 122 remain inserted. In examples, first insertion needle 132 is configured to insert first medical device 120 and second insertion needle 134 is configured to insert second medical device 122 via hole 114.

Insertion device 124 may be implemented in a variety of ways. In the example of FIG. 4, insertion device 124 includes an axle 140 configured to rotate around a longitudinal axis of rotation L ("axis L"). However, it should be appreciated that in some embodiments, an insertion device can be implemented without an axle, and in some other embodiments, an insertion device can be implemented with multiples axles.

In FIG. 4, axis L is depicted perpendicular to the page, although this is not required. Axis L may have any orientation with respect to housing 102 and/or other components of therapy delivery device 100. Insertion device 124 may comprise axle 140 configured to rotate in a first rotational direction R1 around axis L and in a second rotational direction R2 opposite the first rotational direction R1 to cause first insertion needle 132 and second insertion needle 134 to insert first medical device 120 and second medical device 122 respectively.

Insertion device 124 is configured to cause first insertion needle 132 and second insertion needle 134 to extend through hole 114 and toward the user when axle 140 rotates in the first rotational direction R1 and may be configured to cause first insertion needle 132 and second insertion needle 134 to retract through hole 114 and away from the user when axle 140 rotates in the second rotational direction R2. In examples, first insertion needle 132 includes a distal end 142 ("first needle distal end 142") and second insertion needle 134 includes a distal end 144 ("second needle distal end 144").

In some embodiments, insertion device 124 may be a component of therapy delivery device 100. Thus, insertion device 124 may be configured to cause first needle distal end 142 and second needle distal end 144 to move from positions within housing 102 to positions outside housing 102 when axle 140 rotates in the first rotational direction R1, and may be configured to cause first needle distal end 142 and second needle distal end 144 to move from positions outside housing 102 to positions inside housing 102 when axle 140 rotates in the second rotational direction R2. First insertion needle 132 and second insertion needle 134 may be configured to insert first medical device 120 and second medical device 122 respectively within a user when first insertion needle 132 and second insertion needle 134 extend outside of housing 102, and/or configured to release first medical device 120 and second medical device 122 respectively when first insertion needle 132 and second insertion needle 134 retract inside of housing 102, such that first medical device 120 (e.g., a fluid delivery cannula) and second medical device 122 (e.g., an analyte sensor) remain inserted in the user. In examples, first insertion needle 132 and second insertion needle insert first medical device 120 and second medical device 122 substantially concurrently.

In some other embodiments, insertion device 124 may be external to therapy delivery device 100. As will be described in greater detail below, insertion device 124 may comprise housing 126 configured to couple with housing 102 for insertion of medical devices 120 and 122 into the patient.

Insertion device 124 may be configured to cause first needle distal end 142 to travel substantially along the first path S1 when insertion device 124 extends and/or retracts first insertion needle 132. Insertion device 124 may be configured to cause second needle distal end 144 to travel substantially along the second path S2 when insertion device 124 extends and/or retracts second insertion needle 134. In examples, insertion device 124 is configured such that the first path S1 and the second path S2 cause first needle distal end 142 and second needle distal end 144 to increasingly displace from each other as first needle distal end 142 and/or second needle distal end 144 move in a direction away from housing 102. In examples, insertion mechanism unit 124 is configured such that one of first path S1 or second path S2 defines a first curvature around axis L and the other of first path S1 or second path S2 defines a second curvature around axis L. In some embodiments, the second curvature may be less than the first curvature. For example, insertion device 124 may be configured such that first path S1 is substantially circular and second path S2 is substantially linear. In some embodiments, the first curvature and the second curvature may have opposite orientations. For example, the first curvature may be clockwise whereas the second curvature may be counterclockwise. Insertion device 124 may define the first path S1 and the second path S2 in order to generate the displacement D (FIG. 3) between first medical device 120 and second medical device 122 within body 101 of the user.

Insertion device 124 may be configured to cause first needle distal end 142 and second needle distal end 144 to pass through hole 114 as first needle distal end 142 and second needle distal end 144 transition to the positions in the patient. In examples, insertion device 124 is configured to cause first needle distal end 142 and second needle distal end 144 to pass through an insertion area 149 on the skin 118 (FIG. 2) of the patient. Insertion area 149 may be a relatively small area on the skin of the patient, such that the patient only perceives a single piercing action from the penetration of both first insertion needle 132 and second insertion needle 134. In some examples, insertion device 124 is configured to cause first insertion needle 132 and second insertion needle 134 to insert through the skin of the patient through substantially the same puncture site on the skin of the patient. For example, one of first insertion needle 132 or second insertion needle 134 may be configured to initially pierce and insert through the skin at the puncture site, and the other of first insertion needle 132 or second insertion needle 134 may be configured to subsequently insert through the skin through substantially the same puncture site.

Insertion device 124 further includes a driver 150 configured to cause the rotation of axle 140 in the first rotational direction R1 and/or the second rotational direction R2. In examples, driver 150 is configured to cause axle 140 to initially rotate in the first rotational direction R1 and subsequently in the second rotational direction R2 (e.g., to cause initial extension of insertion needles 132, 134 followed by subsequent retraction of insertion needles 132, 134). For example, driver 150 may be configured to initially cause first needle distal end 142 and/or second needle distal end 144 to move from a position within housing 102 to a position outside of housing 102 (e.g., by initially rotating axle 140 in the first rotational direction R1), and configured to subsequently cause first needle distal end 142 and/or second needle distal end 144 to move from a position outside housing 102 to a position within housing 102 (e.g., by subsequently rotating axle 140 in the second rotational direction R2). In examples, user input device 108 is configured to cause driver 150 to rotate axle 140 in the first rotational direction R1 and/or the second rotational direction R2, such that the user may control the implantation of first medical device 120 and second medical device 122. In some examples, as will be discussed, driver 150 may include one or more springs configured to cause axle 140 to rotate around axis L. In some examples, driver 150 includes a first spring configured to rotate axle 140 in the first rotational direction R1 and a second spring configured to rotate axle 140 in the second rotational direction R2. In some examples, each spring is a torsion spring configured to release from a loaded configuration to an unloaded configuration and/or vice versa to cause axle 140 to rotate around axis L.

In examples, therapy delivery device 100 comprises a first conduit 156 that defines a first flow path 152 from a discharge 153 of fluid pump 136 to first medical device 120. In examples, first medical device 120 is a fluid delivery cannula defining an interior lumen 154, and first conduit 156 is configured to define first flow path 152 from a discharge 153 of fluid pump 136 through lumen 154 of the fluid delivery cannula. Therapy delivery device 100 may be configured to accommodate a fluid reservoir 158 (e.g., within device housing 102 and/or fluid cartridge 104 (FIGS. 1, 2)). In examples, therapy delivery device 100 includes a second conduit 162 configured to define second flow path 160 from reservoir 158 to a suction 161 of fluid pump 136.

Fluid pump 136 may include motor 138 configured to cause fluid pump 136 to create pressure to deliver fluid (e.g., via first flow path 152). Fluid infusion system 128 may include one or more of fluid pump 136, motor 138, first conduit 156, fluid reservoir 163, and/or second conduit 162.

Therapy delivery device 100 may include one or more of a processor device 166; one or more of a memory element 168 to store and/or maintain data, processor-readable program instructions; one or more of a battery 170 or other power source; and/or a sensor interface 173 configured to establish electrical connectivity with a medical device, such as second medical device 122. Processor device 166, memory element 168, battery 170, and/or sensor interface 173 may be included on an electronics assembly 171 (e.g., a printed circuit board). In examples, second medical device 122 is an analyte sensor configured to be electrically connected to sensor interface 173 (e.g., via conductive wires) to establish electrical connectivity between conductors of the analyte sensor and conductors of the electronics assembly 171. Electronics assembly 171 (or the components of electronics assembly 171) can be electrically connected to other elements of therapy delivery device 100 as needed to support the operation of therapy delivery device 100. For example, the electronics assembly 171 can be electrically connected to at least the following, without limitation: the fluid pump 136; the sensor interface 173; the insertion device 124; and the user input device 108. It should be appreciated that electrical connections to the electronics assembly 171 can be direct or indirect if so desired. Moreover, one or more components of the electronics assembly 171 may support wireless data communication in some embodiments.

In examples, processor device 166 includes processing circuitry configured to control an operation of fluid pump 136. For example, the processing circuitry may be configured to cause the fluid pump 136 to commence, continue, and/or cease causing transportation of fluid from fluid reservoir 158 to first medical device 120 (e.g., a fluid delivery cannula).

In examples, first medical device 120 and/or second medical device 122 is an analyte sensor configured to generate a signal indicative of a physiological characteristic of the user (e.g., a glucose level), and the processing circuitry is configured to determine the physiological characteristic using the indicative signal. In some examples, the processing circuitry is configured to control an operation of fluid pump 136 based on the indicative signal reported by the analyte sensor. The analyte sensor may be coupled to sensor system 130. Sensor system 130 may also include sensor interface 173 and conductive wires for connecting the analyte sensor to sensor interface 173.

Device housing 102 may be suitably shaped, sized, and configured to house or support the electronics assembly 171, the fluid pump 136, the fluid reservoir 158, the sensor interface 173, and/or the user input device 108. The fluid infusion system 128 depicted in FIG. 3 may include at least the fluid pump 136, the fluid reservoir 158, first conduit 156, and second conduit 162 shown in FIG. 4. The sensor system 130 depicted in FIG. 3 may include at least the sensor interface 173 shown in FIG. 4.

Figure 5C:
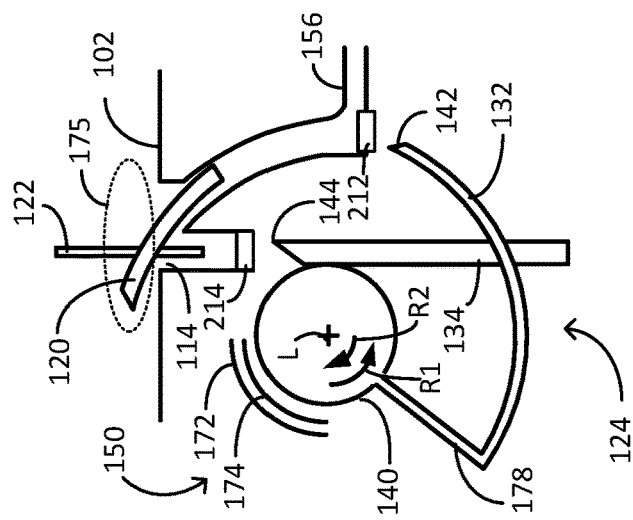
FIG. 5C is a schematic of the insertion device of FIG. 5A and FIG. 5B in a stowed configuration.
Figure 5B:
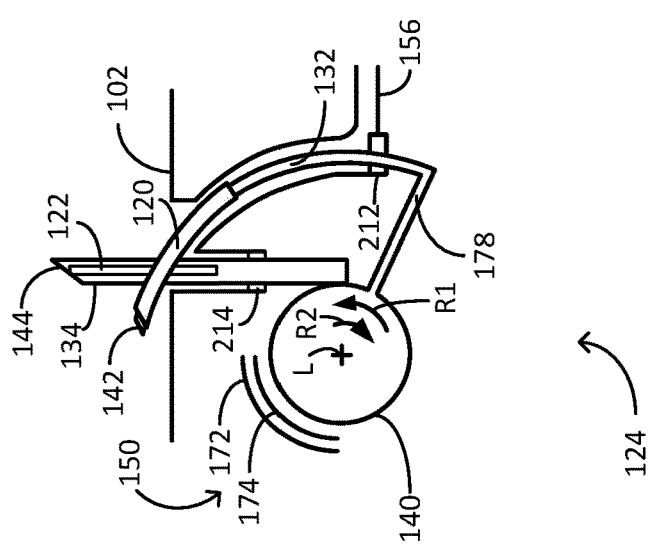
FIG. 5B is a schematic of the insertion device of FIG. 5A in a deployed configuration.
Figure 5A:
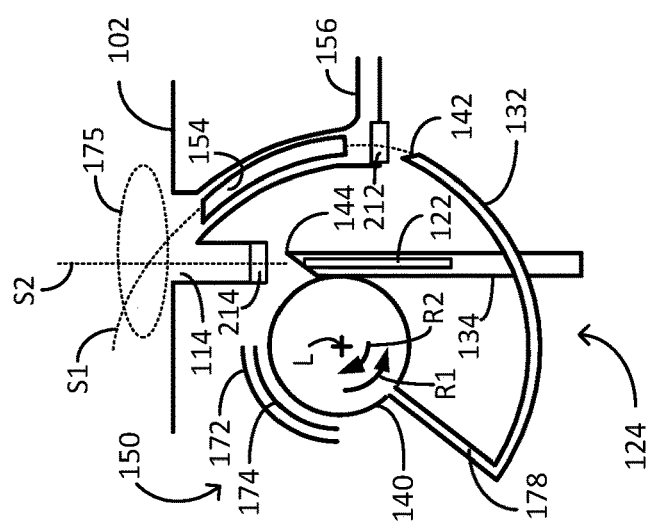
FIG. 5A is a schematic of an example insertion device in an undeployed configuration.

FIG. 5A, FIG. 5B, and FIG. 5C schematically illustrate interaction between a portion of therapy delivery device 100 and insertion device 124. Insertion device 124 may include axle 140 configured to cause first insertion needle 132 to extend and/or retract through hole 114 in housing 102 and configured to cause second insertion needle 134 to extend and/or retract through hole 114 in housing 102. Axis L is included for reference. Driver 150 may be configured to rotate axle 140 in the first rotational direction R1 to cause insertion device 124 to transition from the configuration of FIG. 5A to the configuration of FIG. 5B, in order to cause insertion needles 132, 134 to extend through hole 114 in housing 102. Driver 150 may be configured to rotate axle 140 in the second rotational direction R2 to cause insertion device 124 to transition from the configuration of FIG. 5B to the configuration of FIG. 5C, in order to cause insertion needles 132, 134 to retract through hole 114 in housing 102. First insertion needle 132 and second insertion needle 134 may be configured to release first medical device 120 and second medical device 122 respectively, such that first medical device 120 and second medical device 122 remain inserted in the user when insertion needles 132, 134 are retracted by insertion device 124. In examples, driver 150 includes a first spring 172 configured to cause axle 140 to rotate in the first rotational direction R1 and a second spring 174 configured to cause axle 140 to rotate in the second rotational direction R2.

Axle 140 may be configured to drive first insertion needle 132 to cause first needle distal end 142 to insert through the skin of the user when axle 140 rotates in the first rotational direction R1 around axis L. First insertion needle 132 may be configured such that movement of first needle distal end 142 defines a curved path S1 around axis L when axle 140 drives first insertion needle 132 to insert through the skin of the user. In examples, first insertion needle 132 is a curved needle substantially curving around axis L. First insertion needle 132 may be configured such that, as axle 140 drives first insertion needle 132 through the skin, first needle distal end 142 substantially tunnels through tissue of the user in a curved path (e.g., the path S1) relative to axis L. In examples, when axle 140 rotates in the first rotational direction R1 around axis L, insertion device 124 causes first insertion needle 132 to rotate in the first rotational direction R1 around axis L. In examples, insertion device 124 is configured to cause first insertion needle 132 to engage first medical device 120 when axle 140 rotates in the first rotational direction R1. For example, first insertion needle 132 may become progressively narrower toward distal end 142 such that rotation of axle 140 causes needle 132 to be inserted through lumen 154 until first medical device 120 makes contact with needle 132. As will be discussed, first insertion needle 132 may be configured to engage first medical device 120 to displace at least some portion of first medical device 120 from a position within housing 102 (e.g., a position within first conduit 156 as depicted in FIG. 5A) to a position outside of housing 102 (e.g., as depicted in FIG. 5B).

Axle 140 may be configured to impart a torque around axis L to an insertion needle (e.g., first insertion needle 132 and/or second insertion needle 134) curving around the axis L. For example, in FIGS. 5A-5C, axle 140 is configured to impart a torque around axis L to first insertion needle 132 curving around the axis L. Axle 140 may impart the torque such that first insertion needle 132 substantially rotates around axis L when the axle 140 rotates around axis L. In examples, axle 140 is mechanically connected to first insertion needle 132 to impart the torque. For example, axle 140 may be mechanically connected to first insertion needle by a strut 178 extending between axle 140 and first insertion needle 132, however this is not required. Axle 140 may impart the torque around axis L to first insertion needle 132 in any manner. In some examples, a surface of axle 140 is configured to frictionally engage a surface of first insertion needle 132, such that the frictional engagement causes axle 140 to impart the torque to first insertion needle 132. In some examples, axle 140 may be configured to rotate a pinion gear meshed with a curved rack gear coupled to first insertion needle 132, such that the meshing causes axle 140 to impart the torque to first insertion needle 132.

Axle 140 may be further configured to drive second insertion needle 134 to cause second needle distal end 144 to insert through the skin of the user when axle 140 rotates in the first rotational direction R1 around axis L. In examples, second insertion needle 134 is a substantially straight needle configured to exhibit a linear motion relative to housing 102 when axle 140 rotates around axis L. Second insertion needle 134 may be configured such that movement of second needle distal end 144 defines a path S2 when axle 140 drives second insertion needle 134 to insert through the skin of the user. In examples, the path S2 has a different curvature (e.g., a reduced curvature) relative to axis L compared to the path S1. In some examples, the path S2 is a substantially linear path. Second insertion needle 134 may be configured such that, as axle 140 drives second insertion needle 134 through the skin, second needle distal end 144 substantially tunnels through tissue of the user substantially along the path S2. Second insertion needle 134 may be configured to engage second medical device 122 to displace at least some portion of second medical device 122 from a position within housing 102 (e.g., as depicted in FIG. 5A) to a position outside of housing 102 (e.g., as depicted in FIG. 5B). For example, second insertion needle 134 may have a hollow portion toward distal end 144, and an opening may be defined in distal end 144 such that rotation of axle 140 causes needle 134 to accommodate second medical device 122 within the hollow portion.

In examples, axle 140 is configured to impart a substantially linear force to an insertion needle (e.g., first insertion needle 132 and/or second insertion needle 134). For example, in FIGS. 5A-5C, axle 140 is configured to impart the substantially linear force to second insertion needle 134 to cause second needle distal end 144 to travel along the path S2. Axle 140 may impart the substantially linear force when axle 140 rotates around axis L. In examples, axle 140 is operatively connected to second insertion needle 134 to impart the substantially linear force. In some examples, axle 140 is configured to cause the rotation of a pinion gear (e.g., pinion gear 180 (FIG. 6)) meshed with a rack gear (e.g., rack gear 182 (FIG. 6)) coupled to second insertion needle 134, however this is not required. Axle 140 may impart the substantially linear force to second insertion needle 134 in any manner, including any manner of mechanism configured to convert a rotational torque of axle 140 to a substantially linear force on second insertion needle 134. In some examples, a surface of axle 140 is configured to frictionally engage a surface of second insertion needle 134, such that the frictional engagement causes axle 140 to impart the substantially linear force to second insertion needle 134.

Figure 6:
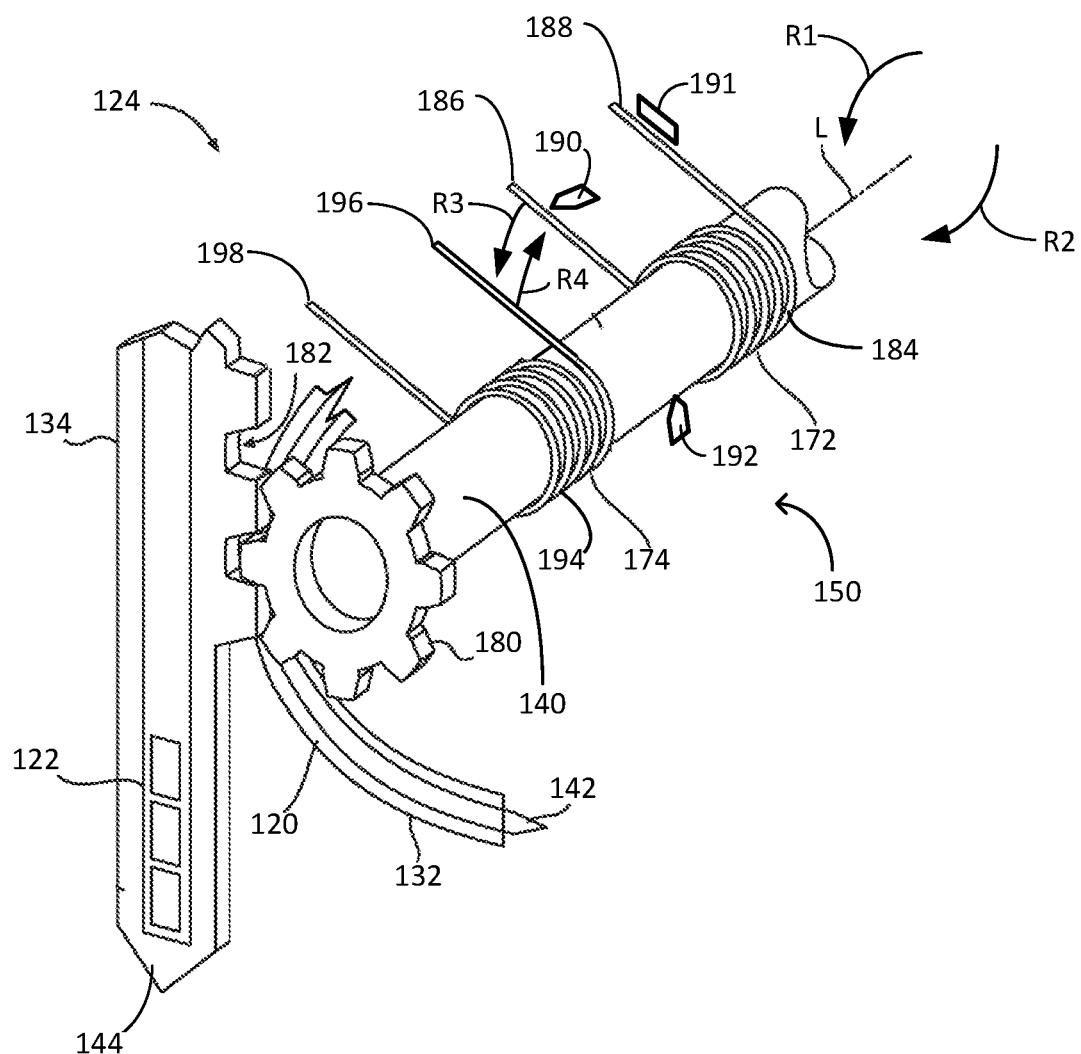
FIG. 6 is a perspective view of an example insertion device.

FIG. 6 schematically illustrates an example of an insertion device 124 including a driver 150. In the example of FIG. 6, driver 150 includes first spring 172 configured to cause axle 140 to rotate relative to housing 102 in the first rotational direction R1. First spring 172 may be configured to convert potential energy into kinetic energy to cause the rotation. For example, first spring 172 may be in a charged (e.g., wound or loaded) condition storing potential energy, and may convert some portion of the potential energy to kinetic energy (e.g., by fully or partially unwinding or unloading) to cause axle 140 to rotate in the first rotational direction R1. Insertion device 124 may be configured such that the full or partial unwinding or unloading of first spring 172 transitions insertion device 124 from the configuration of FIG. 5A to the configuration of FIG. 5B. In examples, first spring 172 is a torsion spring configured to rotate around axis L in the first rotational direction R1 when first spring 172 converts potential energy to kinetic energy. First spring 172 may be mechanically engaged with axle 140, such that rotation of first spring 172 around axis L in the first rotational direction R1 causes rotation of axle 140 in the first rotational direction R1. In examples, first spring 172 includes a helical coil 184 ("first helical coil 184") surrounding axis L and configured to rotate around axis L. In examples, first helical coil 184 surrounds axle 140. Axle 140 may be mechanically engaged with first spring 172 (e.g., first helical coil 184) such that, when first spring 172 rotates around axis L, spring 172 imparts a first torque around axis L to axle 140.

In examples, first spring 172 is a torsion spring having a primary end 186 ("first spring primary end 186") and a secondary end 188 ("first spring secondary end 188"). The torsion spring may be configured to store potential energy by substantially winding (e.g., twisting around) a spring axis, and may be configured to cause movement of first spring primary end 186 relative to first spring secondary end 188 as the torsion spring unwinds to expend the potential energy. The spring axis may be substantially parallel to and/or coincident with axis L. First spring 172 may be configured to exert the first torque on axle 140 when first spring primary end 186 moves relative to first spring secondary end 188. In examples, first spring 172 is configured to cause first spring primary end 186 to move relative to first spring secondary end 188 in the rotational direction R3 around axis L when first spring 172 expends potential energy. The rotational direction R3 may be similar or substantially the same as first rotational direction R1. In some examples, first spring secondary end 188 is coupled to a support structure 191 configured to be substantially stationary with respect to housing 102 such that motion of first spring primary end 186 relative to support structure 191 causes the relative motion between first spring primary end 186 and first spring secondary end 188.

In examples, insertion device 124 includes a release mechanism unit configured to substantially maintain a position of first spring primary end 186 relative to first spring secondary end 188 such that first spring 172 is constrained from exerting a torque on axle 140 until user input device 108 (FIGS. 1, 3, 4) is actuated. When user input device 108 is actuated, insertion device 124 may be configured to allow first spring primary end 186 to move relative to first spring secondary end 188, such that first spring 172 (e.g., first helical coil 184) imparts a torque to axle 140 causing axle 140 to rotate around axis L in the first rotational direction R1. For example, insertion device 100 may include a mechanical stop 190 configured to mechanically engage first spring 172 (e.g., first spring primary end 186) to constrain movement of first spring primary end 186 relative to first spring secondary end 188, such that first spring 172 is substantially preventing from exerting a torque on axle 140. Mechanical stop 190 may be configured to mechanically disengage from spring 172 (e.g., first spring primary end 186), such that spring 172 is free to cause first spring primary end 186 to move in the rotational direction R3 relative to first spring secondary end 188, and such that first spring 172 exerts a torque in the first rotational direction R1 on axle 140.

In some examples, instead of or in addition to mechanical stop 190, insertion device 124 may include a mechanical stop 192 configured to substantially prevent the rotation of axle 140 in the first rotational direction R1, such that axle 140 resists a torque imparted by first spring 172. Mechanical stop 192 may be configured to mechanically disengage from axle 140, such the torque imparted by spring 172 causes rotation of axle 140. In examples, mechanical stop 190 and/or 192 is configured to establish a first position wherein spring 172 is constrained from causing a rotation of axle 140, and configured to establish a second position wherein spring 172 is not constrained from causing a rotation of axle 140. User input device 108 may be configured to cause mechanical stop 190 and/or 192 to transition from the first position to the second position. User input device 108 may be coupled with mechanical stop 190, 192 wirelessly, electrically, mechanically or in any other effective way.

Driver 150 including first spring 172 and/or second spring 174 is one example of a driver configured to cause rotation of axle 140. Driver 150 may cause the rotation of axle 140 in any manner. In examples, driver 150 includes one or more motors configured to cause the rotation of axle 140. The one or more motors may be, for example, a rotary motor configured to cause the rotation using a rotation of an output shaft, a linear motor configured to cause the rotation using translation of a slider, or other type of motors configured to produce an output motion (e.g., relative to a motor housing) and use the output motion to cause the rotation. The one or more motors may be constant or variable speed motors, and may be configured to cause the rotation of axle 140 at a constant rotational speed or a varying rotational speed. In examples, the one or more motors are be configured to receive power from a battery (e.g., battery 170 within therapy delivery device 100). Insertion device 124 and/or therapy delivery device 100 may include processing circuitry configured to control the one or motors (e.g., configured to cause a motor to generate motion, to cease generating motion, to generate motion at a particular speed, etc.) In examples, user input device 108 is configured to actuate the one or more motors to cause the rotation of axle 140.

FIG. 5B illustrates driver 150 having caused axle 140 to rotate in the first rotational direction R1. In FIG. 5B, the rotation of axle 140 in the first rotational direction R1 has caused first insertion needle 132 and second insertion needle 134 to extend from housing 102 such that first needle distal end 142 and second needle distal end 144 achieve positions outside of housing 102. Further, in FIG. 5B, the rotation of axle 140 in the first rotational direction R1 has caused first insertion needle 132 to displace first medical device 120 from an initial position wherein first medical device 120 is within housing 102 (FIG. 5A) to an at least partially implanted position wherein at least some portion of first medical device 120 is outside of housing 102. In FIG. 5B, the rotation of axle 140 in the first rotational direction R1 has also caused second insertion needle 134 to displace second medical device 122 from an initial position wherein second medical device 122 is within housing 102 (FIG. 5A) to an at least partially implanted position wherein at least some portion of second medical device 122 is outside of housing 102.

Driver 150 may be configured such that, after driver 150 has caused first insertion needle 132 and second insertion needle 134 to extend from housing 102 (e.g., FIG. 5B), driver 150 causes first insertion needle 132 and second insertion needle 134 to retract into housing 102 (FIG. 5C). In examples, driver 150 is configured such that, after axle 140 has rotated in the first rotational direction R1 a certain amount (e.g., to extend insertion needles 132, 134), driver 150 causes axle 140 to subsequently rotate in the second rotational direction R2 (e.g., to retract insertion needles 132, 134). User input device 108 may be configured to cause driver 150 to extend and/or retract insertion needles 132, 134, such that the user may control the insertion and/or retraction.

In examples, driver 150 includes second spring 174 (FIGS. 5A-5C, 6) configured to cause axle 140 to rotate relative to housing 102 in the second rotational direction R2 to cause the retraction of first insertion needle 132 and second insertion needle 134 into housing 102. Second spring 174 may be configured to convert potential energy into kinetic energy to cause the rotation. For example, second spring 174 may be charged and/or put into a charged (e.g., wound or loaded) condition having a potential energy, and may convert some portion of the potential energy to kinetic energy (e.g., by fully or partially unwinding or unloading) to cause axle 140 to rotate in the second rotational direction R2. Insertion device 124 may be configured such that the full or partial unwinding of second spring 174 transitions insertion device 124 from the configuration of FIG. 5B to the configuration of FIG. 5C. In examples, second spring 172 is a torsion spring configured to rotate around axis L in the second rotational direction R2 when second spring 174 converts potential energy to kinetic energy. Second spring 174 may be mechanically engaged with axle 140, such that rotation of second spring 174 around axis L in the second rotational direction R2 causes rotation of axle 140 in the second rotational direction R2. Second spring 174 may include a helical coil 194 ("second helical coil 194") surrounding axis L and configured to rotate around axis L. In examples, second helical coil 194 surrounds axle 140. Axle 140 may be mechanically engaged with second spring 174 (e.g., second helical coil 194) such that, when second spring 172 rotates around axis L, spring 172 imparts a second torque around axis L to axle 140. In examples, the second torque imparted by second spring 174 has a rotational direction substantially opposite the rotational direction of the first torque imparted by first spring 172.

In examples, second spring 174 is a torsion spring having a primary end 196 ("second spring primary end 196") and a second spring secondary end 198 ("second spring secondary end 198"). The torsion spring may be configured to store potential energy by substantially winding (e.g., twisting around) a spring axis of second spring 174, and may be configured to cause movement of second spring primary end 196 relative to second spring secondary end 198 as the torsion spring unwinds to expend the potential energy. The spring axis of second spring 174 may be substantially parallel to and/or coincident with axis L. Second spring 174 may be configured to exert the second torque on axle 140 when second spring primary end 196 moves relative to second spring secondary end 198. In examples, second spring 174 is configured to cause second spring primary end 196 to move relative to second spring secondary end 198 in the rotational direction R4 around axis L when second spring 174 expends potential energy. The rotational direction R4 may be similar or substantially the same as second rotational direction R2.

In examples, insertion device 124 is configured to substantially prevent motion of second spring primary end 196 relative to second spring secondary end 198 as axle 140 to rotates in the first rotational direction, such that second spring 174 enters and/or remains in a wound condition. Stated differently, insertion device 124 may be configured to substantially prevent motion of second spring primary end 196 relative to second spring secondary end 198 as first spring 172 unwinds to rotate axle 140.

Figure 7C:
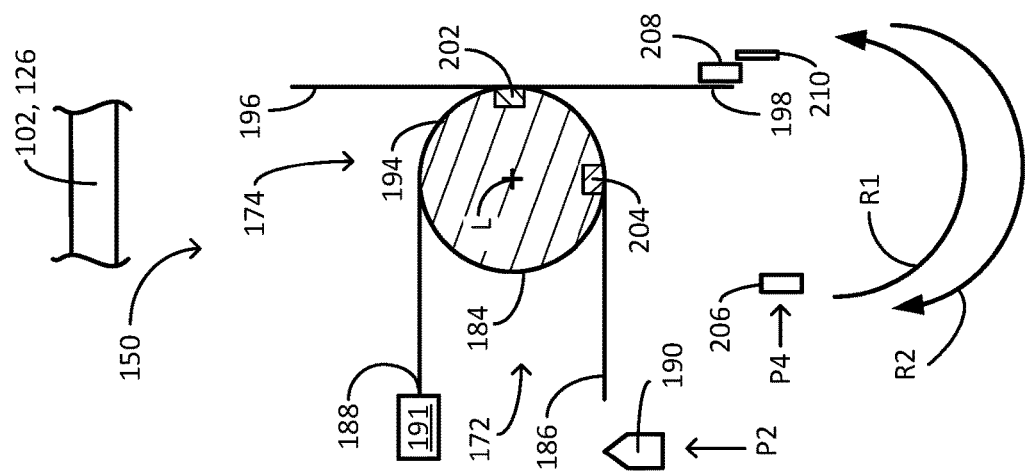
FIG. 7C is a schematic of the example insertion device of FIG. 7A and FIG. 7B in a third configuration.
Figure 7B:
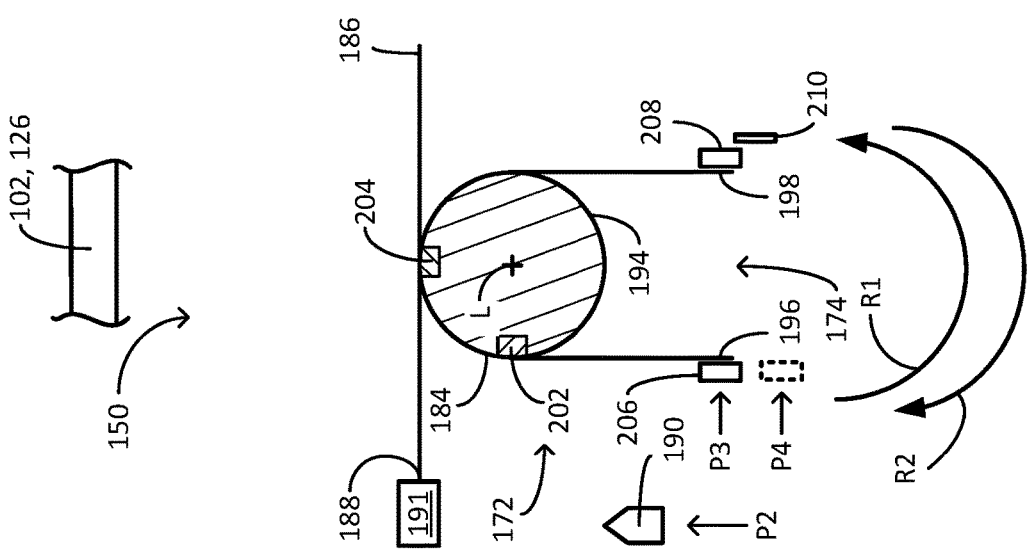
FIG. 7B is a schematic of the example insertion device of FIG. 7A in a second configuration.
Figure 7A:
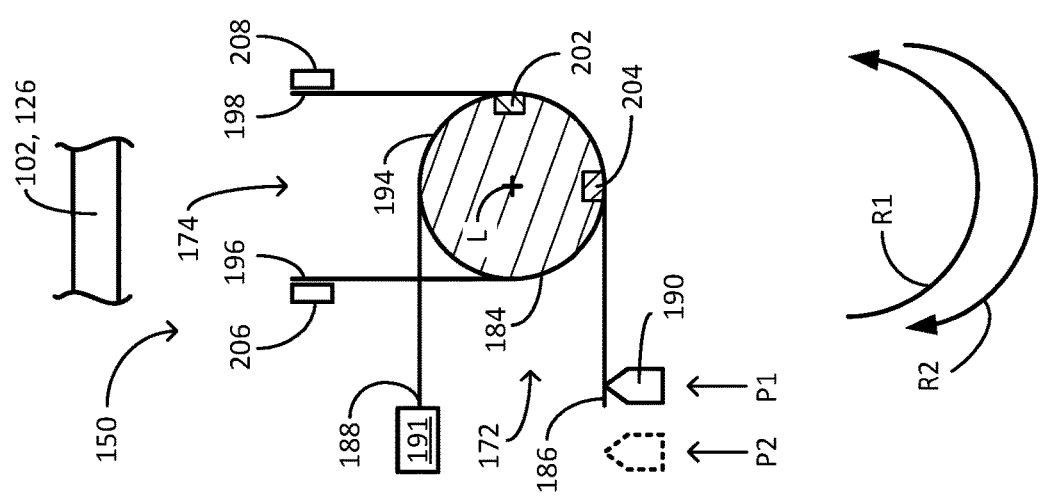
FIG. 7A is a schematic of an example insertion device in a first configuration.

For example, FIGS. 7A, 7B, and 7C illustrate an example driver 150 including first spring 172 and second spring 174.

First spring 172 includes first spring primary end 186 and first spring secondary end 188. First helical coil 184 surrounds axle 140 and is mechanically engaged to axle 140 by fixation structure 202 ("first fixation structure 202"), such that rotation of first helical coil 184 around axis L causes a rotation of axle 140 around axis L. Second spring 174 includes second spring primary end 196 and second spring secondary end 198. Second helical coil 194 surrounds axle 140 and is mechanically engaged to axle 140 by fixation structure 204 ("second fixation structure 204"), such that rotation of second helical coil 194 around axis L causes a rotation of axle 140 around axis L. First spring 172 is configured to cause axle 140 to rotate in the first rotational direction R1 when first spring primary end 186 moves relative to first spring secondary end 188. Second spring 174 is configured to cause axle 140 to rotate in the second rotational direction R2 when second spring primary end 196 moves relative to second spring secondary end 198. Axle 140 is configured to rotate around axis L. Axle 140, first fixation structure 202, and second fixation structure 204 are illustrated as cross-sections with a cutting plane parallel to the page.

FIG. 7A illustrates first spring 172 with support structure 191 engaged (e.g., mechanically engaged) with first spring secondary end 188 to substantially limit motion of first spring secondary end 188 with respect to housing 102. Mechanical stop 190 is in a first position P1 to engage (e.g., mechanically engage) first spring primary end 186, such that mechanical stop 190 substantially prevents movement of first spring primary end 186 relative to first spring secondary end 188 in the first position P1. A mechanical stop 206 is engaged (e.g., mechanically engaged) with second spring primary end 196 and a mechanical stop 208 is engaged (e.g., mechanically engaged) with second spring secondary end 198. Mechanical stops 206, 208 substantially prevent movement of second spring primary end 196 relative to second spring secondary end 198.

FIG. 7B illustrates mechanical stop 190 having repositioned from the first position P1 to a second position P2. In the second position P2, mechanical stop 190 disengages from first spring 172 (e.g., first spring primary end 186), such that the potential energy of first spring 172 may cause first spring primary end 186 to move relative to first spring secondary end 188. FIG. 7B illustrates first spring primary end 186 having moved around axle 140 in the first rotational direction R1 relative to first spring secondary end 188. The movement of first spring primary end 186 has caused first spring 172 to exert a first torque on axle 140, causing axle 140 to rotate in the first rotational direction R1. Mechanical stops 206, 208 are configured to rotate around axis L in the first rotational direction R1 when axle 140 rotates in the first rotational direction R1, such that mechanical stops 206, 208 substantially prevent second spring 174 from unwinding to expend potential energy as axle 140 rotates in the first rotational direction R1. In FIG. 7B, mechanical stop 206 is in a first position P3 to engage second spring 174 (e.g., second spring primary end 196) and substantially prevents movement of first spring primary end 186 relative to first spring secondary end 188.

FIG. 7C illustrates mechanical stop 190 having repositioned from the first position P3 to a second position P4. In the second position P4, mechanical stop 206 disengages from second spring 174 (e.g., second spring primary end 196), such that the potential energy of second spring 174 may cause second spring primary end 196 to move relative to second spring secondary end 198. FIG. 7C illustrates second spring primary end 196 having moved around axle 140 in the second rotational direction R2 relative to second spring secondary end 188. The movement of second spring primary end 196 has caused second spring 174 to exert a second torque on axle 140, causing axle 140 to rotate in the second rotational direction R2.

Driver 150 may be configured to cause axle 140 to rotate in the first rotational direction R1 (e.g., to cause extension of insertion needles 132, 134 (FIGS. 4, 5A-5C, 6)) and/or configured to cause axle 140 to rotate in the second rotation direction R2 (e.g., to cause retraction of insertion needles 132, 134). In examples, driver 150 is configured to cause the rotation in the second rotational direction R2 after axle 140 has rotated in the first rotational direction R1 by a certain amount. For example, driver 150 may include a limit switch 210 configured to cause second spring 174 to exert the second torque on axle 140 when axle 140 has rotated by the certain amount. In examples, limit switch 210 is configured to cause mechanical stop 206 to transition from the first position P3 to the second position P4 when axle 140 rotates the certain amount. Limit switch 210 may be, for example, a mechanical switch configured to be actuated by some portion of second spring 174 (e.g., second spring secondary end 198) and/or axle 140 when axle 140 has rotated the certain amount. In other examples, limit switch 210 may be a proximity switch such as a magnetic switch configured by a proximity of second spring 174 and/or axle 140 to limit switch 210. In some examples, limit switch 210 may be a position sensor configured to sense a position of second spring 174 and/or axle 140.

Second spring 174 may be configured to cause axle 140 and thus first spring 172 to rotate in the second rotational direction R2. Insertion device 124 may be configured such that first spring 172 substantially rewinds (e.g., stores potential energy) when axle 140 rotates in the second rotational direction R2. In examples, second spring 174 is configured to cause first spring 172 to store potential energy when second spring 174 causes axle 140 to rotate in the second rotational direction. In some examples, first spring 172 has a first torsion spring rate over the certain amount of axle 140 rotation and second spring 174 has a second torsion spring rate over the certain amount of axle 140 rotation, and the second torsion spring rate of second spring 174 is greater than the first torsion spring rate of first spring 172.

User input device 108 (FIGS. 1, 3, 4) may be configured to cause mechanical stop 190 to reposition from first position P1 to second position P2, such that driver 150 causes the extension of insertion needles 132, 134. User input device 108 may be configured to cause mechanical stop 206 to reposition from first position P3 to second position P4, such that driver 150 causes the retraction of insertion needles 132, 134. In examples, user input device 108 may be configured to cause mechanical stop 190 to reposition from first position P1 to second position P2, such that driver 150 causes the extension and/or retraction of insertion needles 132, 134. Further, although FIGS. 7A-7C illustrate rotations of axle 140 in the first rotational direction R1 and the second rotational direction R2 of about 180 degrees, driver 150 may be configured to cause rotation of axle 140 by any amount in the first rotational direction R1 and/or the second rotational direction R2. User input device 108 may be coupled with mechanical stop 190, 206 wirelessly, electrically, mechanically or in any other effective way.

Driver 150 may use any elastic object configured to store mechanical energy as potential energy and configured to cause the rotation of axle 140 using an expenditure of the potential energy. Spring 172, 174 may be any type of spring. For example, spring 172, 174 may be torsion spring discussed above, a compression spring, a leaf spring, a spiral spring, a flat spring, a machined spring, a serpentine spring, a garter spring, or another type of spring configured to store potential energy. Spring 172, 174 may be a constant force or variable force spring. Driver 150 may use any number of springs and any type of spring in any combination to cause the rotation of axle 140.

Hence, insertion device 124 may be configured to cause insertion needles 132, 134 to extend away from housing 102 and/or subsequently retract in a direction toward housing 102 when axle 140 rotates relative to housing 102. In examples, insertion device 124 is configured to cause first insertion needle 132 to transition (e.g., along the path S1) from a first undeployed position (FIG. 5A) wherein first needle distal end 142 is within housing 102 to a first deployed position (FIG. 5B) wherein first needle distal end 142 is outside housing 102. In examples, insertion device 124 is configured to cause second insertion needle 134 to transition (e.g., along the path S2) from a second undeployed position (FIG. 5A) wherein second needle distal end 144 is within housing 102 to a second deployed position (FIG. 5B) wherein second needle distal end 144 is outside housing 102. Insertion device 124 may be configured to cause first insertion needle 132 to transition from the first deployed position to a first stowage position (FIG. 5C) wherein first needle distal end 142 is within housing 102. Insertion device 124 may be configured to cause second insertion needle 134 to transition from the second deployed position to a second stowage position (FIG. 5C) wherein second needle distal end 144 is within housing 102. The first stowage position may be a different position than the first undeployed position, or may be substantially the same position as the first undeployed position, and the second stowage position may be a different position that the second undeployed position, or may be substantially the same position as the second undeployed position.

Insertion device 124 may be configured and/or supported within housing 102 to cause the extension and/or retraction of first insertion needle 132 in any direction relative to housing 102. Insertion device 124 may be configured and/or supported within housing 102 to cause the extension and/or retraction of second insertion needle 134 in any direction relative to housing 102. Further, axle 140, first insertion needle 132, second insertion needle 134, first spring 172, second spring 174, and/or other components of insertion device 124 may have any orientation relative to housing 102 and each other sufficient to cause the extension and/or retraction of first insertion needle 132 and second insertion needle 134. Insertion device 124 may be configured to cause the extension and/or retraction of first insertion needle 132 and second insertion needle 134, and at least partial implantation of first medical device 120 and second medical device 122, at any angle relative to housing 102. Insertion device 124 may be configured to cause the extension and/or retraction of first insertion needle 132 and second insertion needle 134, and the at least partial implantation of first medical device 120 and second medical device 122 at any angle relative to the patient when insertion device 124 is proximate the skin 118 of the patient.

Insertion device 124 may be configured to cause the insertion of first insertion needle 132 substantially concurrently with second insertion needle 134, and/or be configured to cause the insertion of first insertion needle 132 sequentially (e.g., before or after) relative to the insertion of second insertion needle 134. Insertion device 124 may be configured to cause the retraction of first insertion needle 132 substantially concurrently with second insertion needle 134, and/or be configured to cause the retraction of first insertion needle 132 sequentially (e.g., before or after) relative to the insertion of second insertion needle 134.

As discussed, first insertion needle 132 may be configured to releasably engage first medical device 120 to cause the at least partial implantation of first medical device 120 within the patient. In examples, first medical device 120 is a fluid delivery cannula configured to deliver a fluid (e.g., insulin) to a user. First insertion needle 132 and the fluid delivery cannula may be cooperatively configured and arranged such that the first insertion needle 132 releasably carries at least a portion (e.g., a distal portion) of the fluid delivery cannula as first insertion needle 132 is caused to extend away from housing 102. In some examples, first insertion needle 132 is configured to extend into lumen 154 of the fluid delivery cannula when first insertion needle 132 extends away from housing 102. First insertion needle 132 and/or the fluid delivery cannula may be configured such that first insertion needle 132 mechanically engages the fluid delivery cannula when first insertion needle 132 (e.g., first needle distal end 142) extends in a direction away from housing 102 and disengages from the fluid delivery cannula when first insertion needle 132 retracts in a direction toward housing 102. (FIGS. 4, 5A-5C).

In examples, when first insertion needle 132 is in the first undeployed position wherein first needle distal end 142 is within housing 102 (FIG. 5A)), insertion device 124 may be configured to maintain separation between first medical device 120 (e.g., the fluid delivery cannula) and first insertion needle 132. For example, insertion device 124 may be configured to maintain separation between first insertion needle 132 and first medical device 120 using a first septum 212 (FIG. 4, 5A-5C). First septum 212 may be a self-sealing material across an aperture defined in first conduit 156. Insertion device 124 may be configured such that, as first insertion needle 132 extends (e.g., along the path S1), insertion needle 132 (e.g., first distal end 142) punctures first septum 212 prior to engaging first medical device 120.

First insertion needle 132 may be configured to engage first medical device 120 to cause at least some portion of first medical device 120 to translate in a direction away from housing 102 (e.g., substantially along the path S1). First insertion needle 132 may be configured to exert a force on first medical device 120 in the direction away from housing 102 to cause the translation of first medical device 120. For example, first insertion needle 132 and/or first medical device 120 may include a first structural feature configured to cause first insertion needle 132 to exert the force in the direction away from housing 102 on first medical device 120 when first insertion needle 132 (e.g., first distal end 142) extends in the direction away from housing 102. In examples, first insertion needle 132 is configured to enter lumen 154 to engage first medical device 120. First insertion needle 132 may be configured to engage first medical device 120 to cause at least partial implantation of first medical device in the patient as first insertion needle 132 extends in the direction away from housing 102 into the patient. First medical device 120 (e.g., a fluid delivery cannula) may be configured to extend from device housing 102 when first insertion needle 132 causes the at least partial implantation of first medical device 120 within the patient. First insertion needle 132 may be configured to disengage from (e.g., release) first medical device 120 when first insertion needle 132 (e.g., first distal end 142) is subsequently retracted in a direction toward housing 102 by insertion device 124. For example, first insertion needle 132 and/or first medical device 120 may include a structural feature (the same as the first structural feature or a different structural feature) configured to allow first insertion needle 132 to move substantially independently of first medical device 120 when insertion device 124 retracts first insertion needle 132 toward housing 102.

In examples, first insertion needle 132 is configured to substantially mate with first medical device 120 when a first insertion needle 132 exerts the force in the direction away from housing 102. First insertion needle 132 may be configured such that a subsequent force toward housing 102 causes first insertion needle 132 to unmate (e.g., disengage) and move independently of first medical device 120. In examples, first insertion needle 132 includes a bearing surface configured such that, when the force in the direction away from housing 102 is exerted on first insertion needle 132, the bearing surface engages a portion of first medical device 120 and transmits some portion of the force to first medical device 120, and when a force toward housing 102 is exerted on first insertion needle 132, the bearing surface disengages the portion of first medical device 120, such that first insertion needle 132 moves independently of first medical device 120. Hence, insertion device 124 may be configured to retract first insertion needle 132 in the direction toward housing 102 independently from first medical device 120, such that first medical device 120 remains at least partially implanted as first insertion needle 132 retracts.

Insertion device 124 may be configured to retract first insertion needle 132 to a first stowage position wherein first needle distal end 142 is within housing 102. Insertion device 124 may retract first insertion needle 132 such that first needle distal end 142 retracts through first septum 212. First septum 212 may be configured to self-seal when first needle distal end 142 retracts in order to establish a fluid-proof barrier between first conduit 156 and other components of therapy delivery device 100, such as driver 150, processor 166 including processing circuitry, memory element 168, and other portions of therapy delivery device 100 which may be adversely impacted by contact with a fluid within first conduit 156.

As discussed, second insertion needle 134 may be configured to releasably engage second medical device 122 to cause the at least partial implantation of second medical device 122 within the patient. In examples, second medical device 122 is an analyte sensor configured to monitor a physiological characteristic (e.g., a glucose level) of the user. Second insertion needle 134 and the analyte sensor may be cooperatively configured and arranged such that the second insertion needle 132 releasably carries at least a portion (e.g., a distal portion) of the analyte sensor as second insertion needle 134 (e.g., second needle distal end 144) extends in a direction away from housing 102. In some examples, second insertion needle 134 is configured to at least partially surround the analyte sensor to carry the analyte sensor as second insertion needle 134 extends away from housing 102. Second insertion needle 134 may be configured as a partially hollow needle defining a void that accommodates the analyte sensor within the void. Second insertion needle 134 and/or the analyte sensor may be configured such that second insertion needle 134 mechanically engages the analyte sensor when second insertion needle 134 extends in the direction away from housing 102 and disengages from the analyte sensor when second insertion needle 134 retracts in a direction toward housing 102.

Second insertion needle 134 may be configured to engage second medical device 122 to cause second medical device 122 to translate in the direction away from housing 102. Second insertion needle 134 may be configured to exert a force on second medical device 122 in the direction away from housing 102 to cause the translation of second medical device 122. Second insertion needle 134 and/or second medical device 122 may include a second structural feature (e.g., the void defined by second insertion needle) configured to cause second insertion needle 134 to exert the force on second medical device 122 when second insertion needle 134 extends in the direction away from housing 102. Second insertion needle 134 may be configured to engage second medical device 122 to cause at least partial implantation of second medical device 122 in the patient as second insertion needle 134 extends in the direction away from housing 102. Second medical device 122 (e.g., an analyte sensor) may be configured to extend from device housing 102 when second insertion needle 134 causes the at least partial implantation of second medical device 122 within the patient.

Second insertion needle 134 may be configured to disengage from (e.g., release) second medical device 122 when second insertion needle 134 is subsequently retracted in the direction toward housing 102. For example, second insertion needle 134 and/or second medical device 122 may include a structural feature (the same as the second structural feature or a different structural feature) configured to allow second insertion needle 134 to move substantially independently of second medical device 122 when insertion device 124 retracts second insertion needle 134 toward housing 102. In some examples, second insertion needle 134 is configured such that body tissue within the patient engages with second medical device 122 (e.g., the analyte sensor) when second insertion needle 134 retracts, such that second medical device 122 remains at least partially implanted in the patient when second insertion needle 134 is withdrawn from the patient. For example, second insertion needle 134 may include a portion (e.g., a distal portion) defining a longitudinal opening, such that a portion of the analyte sensor is exposed to body tissue when second insertion needle 134 and second medical device 122 are inserted in the patient. The body tissue may act to grip (e.g., frictionally engage) the exposed portion of the analyte sensor as second insertion needle 134 is retracted, such that second insertion needle 134 may be retracted into housing 102 as second medical device 122 remains at least partially implanted in the patient. In examples, second medical device 122 (e.g., an analyte sensor) may include one or more structural features configured to assist the frictional engagement with the body tissue.

In examples, therapy delivery device 100 may be configured to prevent ingress of bodily fluid into device 100 via hole 114. This may protect portions of device 100 such as driver 150, processor 166, memory element 168, and others portions of device 100 which may be adversely impacted by contact with a fluid from the user. In examples, device 100 includes second septum 214 (FIG. 4) configured to maintain a fluid-proof barrier between the portions of device 100 and the hole 114. Insertion device 124 may be configured such that, as second insertion needle 134 is extended in the direction away from housing 102, second insertion needle 134 (e.g., second needle distal end 144) punctures second septum 214. Second septum 214 may be comprised of a self-sealing material, such that second septum 214 substantially closes around second insertion needle 134 and/or second medical device 122 to substantially maintain a fluid-proof barrier between the portions of device 100 and the patient.

Insertion device 124 may be configured to retract second insertion needle 134 to the second stowage position, wherein second distal end 142 is within housing 102. Insertion device 124 may retract second insertion needle 134 such that second needle distal end 144 retracts through second septum 214. Second septum 214 may be configured to self-seal (e.g., around second medical device 122) when second needle distal end 144 retracts through second septum 214, in order to substantially maintain a fluid-proof barrier between the components of device 100 and the patient.

As mentioned above, in some embodiments, insertion device 124 may be separate from and external to therapy delivery device 100. Thus, housing 126 of insertion device 124 may be configured to couple with housing 102 of therapy delivery device 100 for insertion of medical devices 120 and 122 into the patient. For example, insertion device 124 may comprise driver 150; axle 140; and needles 132 and 134, whereas therapy delivery device 100 may comprise first conduit 156; septum 212, and septum 214; and medical devices 120 and 122. Referring back to FIG. 5A for visual reference, housing 126 may be mounted on housing 102 such that second insertion needle 134 is aligned with second medical device 122; septum 214; and hole 114, and such that first needle distal end 142 of first insertion needle 132 is aligned with septum 212.

Second medical device 122 may be fabricated using a flexible or pliable substrate or carrier. In examples, second medical device 122 (e.g., an analyte sensor) may be coupled to conductive wires that are initially provided in a folded, serpentine, coiled, or accordion shape to, for example, provide a desired amount of slack to accommodate extension of second medical device 122 while second medical device 122 is electrically coupled to insertion device 124 (e.g., to electronic assembly 171 (FIG. 4). Second medical device 122 may be configured such that, as second insertion needle 134 carries second medical device 122 in a distal direction away from housing 126 (e.g., along the path S2), second medical device 122 extends without losing electrical contact with the electronics assembly 171. In some examples, second medical device 122 is configured to establish electrical coupling (e.g., with electronics assembly 171) after insertion device 124 has been triggered. For example, second medical device 122 may include electrical contact pads configured to electrically connect with one or more connectors of device 100 as or when second insertion needle 132 at least partially implants second medical device 122 within the patient.

Figure 8:
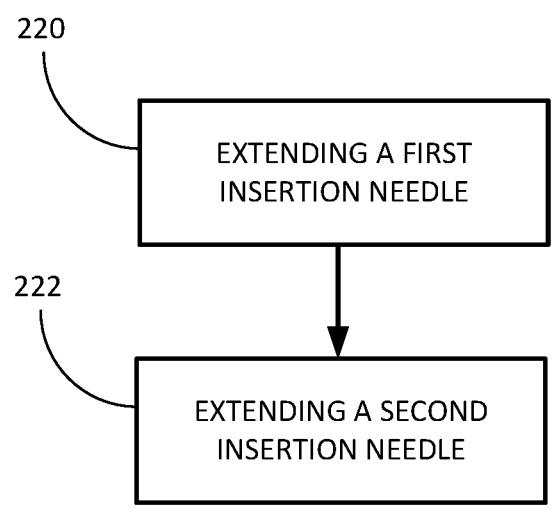
FIG. 8 illustrates an example technique of using an insertion device.

A technique for at least partially implanting a first medical device and a second medical device is illustrated in FIG. 8. Although the technique is described mainly with reference to the various devices of FIG. 1 through FIG. 7C, the technique may be applied to other devices in other examples.

The technique include using a first insertion needle 132 to carry a distal end of a first medical device 120 along a curved path S1 through a hole 114 in an apparatus housing 102 (220). The technique may include rotating an axle 140 with respect to housing 102. Axle 140 may be rotated around a longitudinal axis L in a first rotational direction R1. Axle 140 may be rotated using a driver 150. The technique may include rotating axle 140 in the first rotational direction R1 using a first torque imparted by driver 150. In examples, driver 150 includes a first spring 172. The technique may include exerting the first torque on axle 140 using first spring 172.

The technique includes using a second insertion needle 134 to carry a second medical device 122 through hole 114 (222). The technique may include inserting second insertion needle 134 such that a distal end of second medical device 122 becomes increasingly displaced from the distal end of first medical device 120 as the distal end of first medical device 120 is carried along the curved path.

The technique may include extending first insertion needle 132 and second insertion needle 134 through hole 114 using the rotation of axle 140 in the first rotational direction R1. The technique may include extending the first insertion needle 132 and second insertion needle 134 in a direction away from housing 102. In examples, the technique includes moving a first needle distal end 142 from a first undeployed position within housing 102 to a first deployed position outside of housing 102 using the rotation of axle 140 in the first rotational direction R1. The technique may include causing first needle distal end 142 to move along a path S1. In examples, the technique includes moving a second needle distal end 144 from a second undeployed position within housing 102 to a second deployed position outside of housing 102 using the rotation of axle 140 in the first rotational direction R1. The technique may include causing second needle distal end 144 to move along a path S2. In examples, the path S1 has a first curvature relative to axis L and the path S2 has a second curvature relative to axis L, and the first curvature is greater than the second curvature. In examples, the path S2 is a substantially linear path.

The technique may include exerting a torque around longitudinal axis L on first insertion needle 132 when the axle rotates in the first rotational direction R1. In examples, first insertion needle 132 is a curved needle. The technique may include causing first needle distal end 142 to travel along the path S1 using the torque exerted on first insertion needle 132. In examples, insertion device 124 includes a strut 178 configured to transmit the torque from axle 140 to first insertion needle 132. In examples, insertion device 124 includes a pinion gear coupled to axle 140 and a curved rack gear coupled to first insertion needle 132 such that the pinion gear meshes with the curved rack gear to transfer the torque from axle 140 to first insertion needle 132. In examples, a surface of axle 140 is configured to frictionally engage a surface of first insertion needle 132 to transfer the torque from axle 140 to first insertion needle 132.

The technique may include exerting a substantially linear force on second insertion needle 134 when the axle rotates in the first rotational direction R1. In examples, second insertion needle 134 is a substantially straight needle. The technique may include causing second needle distal end 144 to travel along the path S2 using the substantially linear force exerted on second insertion needle 134. In examples, insertion device 124 is configured to cause a pinion gear 180 to rotate around longitudinal axis L. Pinion gear 180 may be configured to mesh with a rack gear 182 coupled with second insertion needle 134 to exert the substantially linear force on second insertion needle 134. In examples, a surface of axle 140 is configured to frictionally engage a surface of second insertion needle 134 to transfer the substantially linear force to second insertion needle 134.

In examples, the technique includes causing first needle distal end 142 and second needle distal end 144 to extend through a hole 114 defined by housing 102. In examples, the technique includes causing first needle distal end 142 and/or second needle distal end 144 to pierce the skin 118 of the user. The technique may include causing first needle distal end 142 and second needle distal end 144 to insert through the skin 118 of the user within an insertion site 175 on the skin 118 of the user. In examples, the technique includes piercing the skin 118 at a puncture site with one of the first insertion needle 132 or the second insertion needle 134, and inserting the other of the first insertion needle 132 or the second insertion needle 134 through the skin 118 at the puncture site.

The technique may include at least partially implanting a first medical device 120 in the user by extending first insertion needle 132, and at least partially implanting a second medical device 122 in the user by extending second insertion needle 134. In examples, first medical device 120 is a fluid delivery cannula configured to the delivery of a medical fluid (e.g., insulin). In examples, second medical device 122 is an analyte sensor (e.g., a glucose sensor) configured to sense a physiological characteristic of the user (e.g., a glucose level). In examples, insertion device 124 is configured to cause the at least partial implantations such that first medical device 120 and second medical device 122 are separated by a displacement D when at least partially implanted in the user.

The technique may include rotating axle 140 in a second rotational direction R2 substantially opposite the first rotational direction R1. The technique may include retracting first insertion needle 132 and a second insertion needle 134 using the rotation of axle 140 in the second rotational direction R2. The technique may include retracting first insertion needle 132 and second insertion needle 134 in a direction toward housing 102. In examples, the technique includes moving first needle distal end 142 from the first deployed position to a first stowage position inside of housing 102 using the rotation of axle 140 in the second rotational direction R2. The technique may include causing first needle distal end 142 to move along the path S1. In examples, the technique includes moving second needle distal end 144 from the second deployed position to a second stowage position inside of housing 102 using the rotation of axle 140 in the second rotational direction R2. The technique may include causing second needle distal end 144 to move along a path S2.

The technique may include exerting a torque around longitudinal axis L on first insertion needle 132 when the axle rotates in the second rotational direction R2. The technique may include causing first needle distal end 142 to travel along the path S1 using the second torque exerted on first insertion needle 132. The technique may include exerting a substantially linear force on second insertion needle 134 when axle 140 rotates in the second rotational direction R2. The technique may include causing second needle distal end 144 to travel along the path S2 using the substantially linear force exerted on second insertion needle 134.

The technique includes retracting first insertion needle 132 toward housing 102 to withdraw first insertion needle 132 from the user using the rotation of axle 140 in the second rotational direction R2. In examples, the technique includes causing first insertion needle 132 to release first medical device 120 when first insertion needle 132 retracts toward housing 102. The technique may include mechanically disengaging first insertion needle 132 from first medical device 120 such that first medical device 120 remains at least partially implanted in the user when first insertion needle 132 retracts toward housing 102. The technique may include causing first insertion needle 132 to move independently of first medical device 120 during the retraction of first insertion needle 132 such that first medical device 120 remains at least partially implanted in the user when first insertion needle 132 retracts toward housing 102.

The technique includes retracting second insertion needle 134 toward housing 102 to withdraw second insertion needle 134 from the user using the rotation of axle 140 in the second rotational direction R2. In examples, the technique includes causing second insertion needle 134 to release second medical device 122 when second insertion needle 134 retracts toward housing 102. The technique may include mechanically disengaging second insertion needle 134 from second medical device 122 such that second medical device 122 remains at least partially implanted in the user when second insertion needle 134 retracts toward housing 102. The technique may include causing second insertion needle 134 to move independently of second medical device 122 during the retraction of second insertion needle 134 such that second medical device 122 remains at least partially implanted in the user when second insertion needle 134 retracts toward housing 102.

The technique may include rotating axle 140 by exerting a torque on axle 140 using a spring. In examples, the technique includes rotating axle 140 in the first rotational direction R1 by exerting a torque on axle 140 in the first rotational direction R1 using a first spring 172. In examples, the technique includes rotating axle 140 in the second rotational direction R2 by exerting a torque on axle 140 in the first rotational direction R2 using a second spring 174. In examples, the technique includes initially rotating axle 140 in the first rotational direction R1 and subsequently rotating axle 140 in the second rotational direction R2. In examples, driver 150 is configured to initially rotate axle 140 in the first rotational direction R1 and subsequently rotate axle 140 in the second rotational direction R2.

In examples, the technique includes actuating driver 150 using user input device 108 to cause the at least partial implantations of first medical device 120 and second medical device 122. In examples, user input device 108 is configured to cause driver 150 to rotate axle 140 in the first rotational direction R1. In examples, user input device 108 is configured to cause driver 150 to rotate axle 140 in the second rotational direction R2. In examples, user input device 108 is configured to cause driver 150 to initially rotate axle 140 in the first rotational direction R1 and subsequently rotate axle 140 in the second rotational direction R2. In some examples, the technique includes depressing a button on housing 102 to cause user input device 108 to initiate the at least partial implantation of first medical device 120 and second medical device 122. In some examples, the technique includes transmitting an electrical communication to user input device 108 (e.g., a wired or wireless communication) to initiate the at least partial implantation of first medical device 120 and second medical device 122.

Housing 126 may be configured to support at least driver 150, first insertion needle 132, and second insertion needle 134. Housing 126 may be configured to engage (e.g., mechanically engage) device housing 102 of therapy delivery device 100. The technique may including positioning at least first insertion needle 132 and second insertion needle 134 proximate the skin 118 of the user by mounting housing 126 atop housing 102. The technique may include separating housing 126 and housing 102 when first medical device 120 and second medical device 122 are at least partially implanted within the user.

The techniques and functionalities described in this disclosure, including those attributed to processor 166, processing circuitry, sensors, and/or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in any suitable device. Processing circuitry, control circuitry, and sensing circuitry, as well as other processors, controllers, and sensors described herein, may be implemented at least in part as, or include, one or more executable applications, application modules, libraries, classes, methods, objects, routines, subroutines, firmware, and/or embedded code, for example. In addition, analog circuits, components and circuit elements may be employed to construct one, some or all of the control circuitry and sensors, instead of or in addition to the partially or wholly digital hardware and/or software described herein. Accordingly, analog or digital hardware may be employed, or a combination of the two.

In one or more examples, the techniques and functionalities described in this disclosure may be implemented in hardware, software, firmware, or any combination thereof. If implemented in software, the functions may be stored on, as one or more instructions or code, a computer-readable medium and executed by a hardware-based processing unit. The computer-readable medium may be an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

The functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements The present disclosure includes the following examples.

Example 1: An apparatus comprising: a first insertion needle configured to carry a distal end of a first medical device along a curved path that passes through an opening in the apparatus housing; and a second insertion needle configured to carry a distal end of a second medical device through the opening in the apparatus housing, wherein the first insertion needle carries the distal end of the first medical device such that the distal end of the first medical device becomes increasingly displaced from the distal end of the second medical device as the distal end of the first medical device is carried along the curved path.

Example 2: The apparatus of example 1, wherein the first medical device is a fluid delivery conduit and the second medical device is an analyte sensor.

Example 3: The apparatus of example 2, wherein the fluid delivery conduit is a cannula.

Example 4: The apparatus of any of examples 1-3, wherein the second insertion needle is configured to releasably carry the second medical device based on accommodating the second medical device within the second insertion needle.

Example 5: The apparatus of any of examples 1-4, wherein the first insertion needle is configured to releasably carry the first medical device based on being at least partially inserted within a lumen defined by the first medical device.

Example 6: The apparatus of any of examples 1-5, wherein the first insertion needle is configured to release the first medical device when the first insertion needle retracts toward the apparatus housing and the second insertion needle is configured to release the second medical device when the second insertion needle retracts toward the apparatus housing.

Example 7: The apparatus of any of examples 1-6, further comprising an axle configured to rotate around a longitudinal axis of rotation, the axle being configured to cause substantially concurrent passage of the first insertion needle and the second insertion needle through the opening in the apparatus housing when the axle rotates in a first rotational direction around the longitudinal axis.

Example 8: The apparatus of example 7, wherein the second insertion needle comprises a rack gear, wherein the axle is coupled to a pinion gear, and wherein the rack gear is configured to mesh with the pinion gear when the axle rotates around the longitudinal axis.

Example 9: The apparatus of example 7 or 8, further comprising a first torsion spring configured to exert torque on the axle to cause the axle to rotate in the first rotational direction.

Example 10: The apparatus of any of examples 7-9, wherein the axle is configured to cause substantially concurrent retraction of the first insertion needle and the second insertion needle through the opening in the apparatus housing when the axle rotates in a second rotational direction opposite the first rotational direction.

Example 11: The apparatus of example 10, further comprising a second torsion spring configured to cause the axle to rotate in the second rotational direction.

Example 12: The apparatus of example 11, wherein: the first torsion spring has a first spring rate when the axle rotates in the first rotational direction, the second torsion spring has a second spring rate when the axle rotates in the second rotational direction, and the first spring rate is less than the second spring rate.

Example 13: The apparatus of any of examples 1-12, further comprising: a second apparatus housing external to the apparatus housing, the second apparatus housing being configured to engage and disengage the apparatus housing.

Example 14: The apparatus of any of examples 1-13, wherein the second insertion needle is configured to carry the distal end of the second medical device along a second curved path that passes through the opening in the apparatus housing.

Example 15: The apparatus of any of examples 1-14, wherein the first insertion needle is integrated with the first medical device.

Example 16: The apparatus of any of examples 1-15, wherein the second insertion needle is integrated with the second medical device.

Example 17: The apparatus of any of examples 1-16, further comprising: a fluid delivery channel configured to facilitate a fluidic connection between a fluid reservoir and the opening in the apparatus housing; and a septum configured to seal an opening in the fluid delivery channel, wherein the curved path passes through the septum and the opening in the apparatus housing.

Example 18: The apparatus of any of examples 1-17, wherein the second insertion needle is configured to define a substantially straight path that passes through the opening in the apparatus housing.

Example 19: A method comprising: using a first insertion needle to carry a distal end of a first medical device along a curved path through an opening in an apparatus housing; using a second insertion needle to carry a second medical device through the opening in the apparatus housing such that the distal end of the second medical device becomes increasingly displaced from the distal end of the first medical device as the distal end of the first medical device is carried along the curved path.

Example 20: The method of example 19, further comprising rotating an axle in a first rotational direction, wherein the first insertion needle and the second insertion needle are operatively connected to the axle, and wherein the axle is configured to cause substantially concurrent passage of the first insertion needle and the second insertion needle through the opening in the apparatus housing when the axle rotates in the first rotational direction around a longitudinal axis.

Various examples have been described. These are other examples are within the scope of the disclosure.

What is claimed is:

1. An apparatus comprising:
   a first insertion needle configured to carry a distal end of a first medical device along a curved first path that passes through an opening in an apparatus housing, the first path comprising a first length inside of the apparatus housing and a second length outside of the apparatus housing;
   a second insertion needle configured to carry a distal end of a second medical device along a second path that passes through the opening in the apparatus housing, the second path comprising a first length inside of the apparatus housing and a second length outside of the apparatus housing; and,
   an axle configured to rotate around a longitudinal axis, the axle being configured to cause substantially concurrent passage of the first and the second insertion needles through the opening in the apparatus housing when the axle rotates around the longitudinal axis, wherein the first path curves around the longitudinal axis,
   wherein the first and the second paths diverge from one another along their respective second lengths such that the distal end of the first medical device becomes increasingly displaced from the distal end of the second medical device as the distal end of the first medical device is carried along the second length of the first path.

2. The apparatus of claim 1, wherein the first medical device is a fluid delivery conduit and the second medical device is an analyte sensor.

3. The apparatus of claim 2, wherein the fluid delivery conduit is a cannula.

4. The apparatus of claim 1, wherein the second insertion needle is configured to releasably carry the second medical device based on accommodating the second medical device within the second insertion needle.

5. The apparatus of claim 1, wherein the first insertion needle is configured to releasably carry the first medical device based on being at least partially inserted within a lumen defined by the first medical device.

6. The apparatus of claim 1, wherein the first insertion needle is configured to release the first medical device when the first insertion needle retracts toward the apparatus housing and the second insertion needle is configured to release the second medical device when the second insertion needle retracts toward the apparatus housing.

7. The apparatus of claim 1, wherein the second insertion needle comprises a rack gear, wherein the axle is coupled to a pinion gear, and wherein the rack gear is configured to mesh with the pinion gear when the axle rotates around the longitudinal axis.

8. The apparatus of claim 1, further comprising a first torsion spring configured to exert torque on the axle to cause the axle to rotate around the longitudinal axis.

9. The apparatus of claim 1, wherein the axle rotates in a first rotational direction around the longitudinal axis to cause the substantially concurrent passage of the first and the second insertion needles through the opening in the apparatus housing, and wherein the axle is configured to cause substantially concurrent retraction of the first insertion needle and the second insertion needle through the opening in the apparatus housing when the axle rotates in a second rotational direction opposite the first rotational direction.

10. The apparatus of claim 9, further comprising:
    a first torsion spring configured to exert torque on the axle to cause the axle to rotate in the first rotational direction, and
    a second torsion spring configured to cause the axle to rotate in the second rotational direction.

11. The apparatus of claim 10, wherein:
    the first torsion spring has a first spring rate when the axle rotates in the first rotational direction,
    the second torsion spring has a second spring rate when the axle rotates in the second rotational direction, and
    the first spring rate is less than the second spring rate.

12. The apparatus of claim 1, further comprising a second apparatus housing external to the apparatus housing, the second apparatus housing being configured to engage and disengage the apparatus housing.

13. The apparatus of claim 1, wherein the second path is curved.

14. The apparatus of claim 1, wherein the first insertion needle is integrated with the first medical device.

15. The apparatus of claim 1, wherein the second insertion needle is integrated with the second medical device.

16. The apparatus of claim 1, further comprising:
    a fluid delivery channel configured to facilitate a fluidic connection between a fluid reservoir and the opening in the apparatus housing; and
    a septum configured to seal an opening in the fluid delivery channel, wherein the first path passes through the septum and the opening in the apparatus housing.

17. The apparatus of claim 1, wherein the second path is substantially straight.

18. A method comprising:
    using a first insertion needle to carry a distal end of a first medical device along a curved first path through an opening in an apparatus housing, the first path comprising a first length inside of the apparatus housing and a second length outside of the apparatus housing, wherein the first insertion needle is operatively coupled to an axle configured to rotate around a longitudinal axis and the first path curves around the longitudinal axis; and
    using a second insertion needle to carry a second medical device along a second path that passes through the opening in the apparatus housing, the second path comprising a first length inside of the apparatus housing and a second length outside of the apparatus housing, wherein the first and the second paths diverge from one another along their respective second lengths such that the distal end of the second medical device becomes increasingly displaced from a distal end of the first medical device as the distal end of the first medical device is carried along the first path, and wherein the second insertion needle is operatively coupled to the axle, wherein rotation of the axle around the longitudinal axis causes substantially concurrent passage of the first and the second insertion needles through the opening in the apparatus housing.

19. An apparatus comprising:
a first insertion needle configured to carry a distal end of a first medical device along a curved first path that passes through an opening in an apparatus housing, the first path comprising a first length inside of the apparatus housing and a second length outside of the apparatus housing;
a second insertion needle configured to carry a distal end of a second medical device along a linear second path that passes through the opening in the apparatus housing, the second path comprising a first length inside of the apparatus housing and a second length outside of the apparatus housing; and
an axle configured to rotate around a longitudinal axis, the axle being configured to cause substantially concurrent passage of the first and the second insertion needles through the opening in the apparatus housing when the axle rotates around the longitudinal axis,
wherein the first and the second paths diverge from one another along their respective second lengths such that the distal end of the first medical device becomes increasingly displaced from the distal end of the second medical device as the distal end of the first medical device is carried along the second length of the first path.

20. The apparatus of claim 19, wherein the axle rotates in a first rotational direction around the longitudinal axis to cause the substantially concurrent passage of the first and the second insertion needles through the opening in the apparatus housing, and wherein the axle is configured to cause substantially concurrent retraction of the first insertion needle and the second insertion needle through the opening in the apparatus housing when the axle rotates in a second rotational direction opposite the first rotational direction.

* * * * *

UNITED STATES PATENT AND TRADEMARK OFFICE
CERTIFICATE OF CORRECTION

| | |
|---|---|
| PATENT NO. | : 11,806,505 B2 |
| APPLICATION NO. | : 17/109600 |
| DATED | : November 7, 2023 |
| INVENTOR(S) | : Pananen et al. |

Page 1 of 1

It is certified that error appears in the above-identified patent and that said Letters Patent is hereby corrected as shown below:

On the Title Page

Item (56), in Column 2, under "U.S. Patent Documents", Line 1, delete "Yodat" and insert -- Yodfat --, therefor.

Item (56), in Column 2, under "U.S. Patent Documents", Line 2, delete "Yodat" and insert -- Yodfat --, therefor.

In the Claims

In Column 31, in Claim 1, Line 41, delete "and," and insert -- and --, therefor.

Signed and Sealed this
Thirtieth Day of January, 2024

*Katherine Kelly Vidal*

Katherine Kelly Vidal
*Director of the United States Patent and Trademark Office*